US006287563B1

(12) United States Patent
Williams et al.

(10) Patent No.: US 6,287,563 B1
(45) Date of Patent: Sep. 11, 2001

(54) THERAPEUTIC AGENTS AND AUTOIMMUNE DISEASES

(76) Inventors: Neil Andrew Williams, 16 Old Coach Road, Cross, Axbridge, Somerset (GB), BS26 2EF; Timothy Raymond Hirst, 30 Albert Road, Clevedon, North Somerset (GB), BS21 7RR; Toufic Osman Nashar, c/o University of Bristol, School of Medical Services University Walk, Bristol (GB), BS8 1TD (*) Notice: Subject to any disclaimer, the term of this patent is extended or adjusted under 35 U.S.C. 154(b) by 0 days.

(21) Appl. No.: 08/999,458

(22) Filed: Dec. 29, 1997

(30) Foreign Application Priority Data

Jul. 5, 1995 (GB) .................................................. 9513733

(51) Int. Cl.[7] .................................................. H61K 39/00
(52) U.S. Cl. ...................... 424/184.1; 514/885; 530/300; 530/868
(58) Field of Search ........................ 514/2, 885; 530/868; 424/185.1

(56) References Cited

U.S. PATENT DOCUMENTS 5,714,459 * 2/1998 O'Brien et al. ......................... 514/2

FOREIGN PATENT DOCUMENTS 95 10301  4/1995 (WO) .

OTHER PUBLICATIONS

Meyer et al. Presse Medicale, 24 (25) 1171–7, Sep. 1995.*
Wooley et al. Annals of the Rheumatic Diseases, 54 (4) 298–304, Apr. 1995.*
Micusan et al. Seminars in Immunology, 5 (1) 3–11, Feb. 1993.*
Brocke et al. Nature (London), 365(6447), 642–4, Aug. 1993.*
Database CaPlus, DN 121:170050. Ochi, A. CA 2084120, May 1994.*
Database CaPlus, DN 120:75322, Sun, D. J. Neuroimmunol., 46(1–2), 5–10, Jan. 1993.*
Database Medline, AN:84168188. Kaper, J.B. Nature,308 (5960), 655–8, Apr. 1994.*
Proceedings of the National Academy of Sciences of the United States of America 93 (1), 1996, 226–230. Nashar et al. "Potent immunogenicity of the B subunits of *Escherichia coli* heat–labile enterotoxin: Receptor binding is essential and induces differential modulation of lymphocyte subsets". International Immunology 8 (5),1996. 731–736. ISSN: 0953–8178, XP002019423, "Nashar to et al. Cross–linking of cell surface ganglioside GM1 induces the selective apoptosis of mature CD8+ T lymphocytes." see p. 733, right–hand column, last paragraph—p. 735, right–hand column, last line.
The Journal of Immunology, vol. 154, 1995, pp. 3611–3617, XP002019424, B. Yankelevich et al.: "Prevention of Acute Graft–Versus–Host Disease" see pp. 3615–3617, paragraph "Discussion".

(List continued on next page.)

*Primary Examiner*—Michael Borin
(74) *Attorney, Agent, or Firm*—Mary M. Krinsky

(57) ABSTRACT

There is disclosed the use, as an agent in the treatment or the prevention of an autoimmune disease, of:

(i) an agent having GM-1 binding activity, other than Ctx or Etx, or the B subunits of Ctx and Etx; or (ii) an agent having an effect on GM-1 mediated intracellular signalling events, but no GM-1 binding activity.

These agents may also be used in the treatment of human T cell leukaemia, in the prevention of transplant rejection or GVHD or in a vaccination method for vaccinating a mammalian subject.

7 Claims, 11 Drawing Sheets

OTHER PUBLICATIONS

The Journal of Immunology, 154: 1032–1040 (1995), Elson et al.
Microbial, 6: 1949–1958 (1992), Yu et al.
J. Bacteriol, 169: 4570–4576 (1987), Sandkvist et al.
Prot. Express & Purif, 5: 198–204 (1994), Amin et al.
J. Immunol. Meth., 67: 101–108 (1984), Elson et al.
J. Exp. Med. 167: 440–451 (1988), De Aizpura et al.
Curr. Opin. Immunol, 5: 361–367 (1993), Jenkins et al.
J. Immunol. 148: 1999–2005 (1992), Francis et al.
Proc. Natl. Acad. Sci., USA, 72: 3844–3848 (1975), Craig et al.
Proc. Natl. Acad. Sci., 83: 5673–5677 (1986), Imboden et al.
Cancer Res. 53: 4776 (1993), O'Connor et al.

* cited by examiner

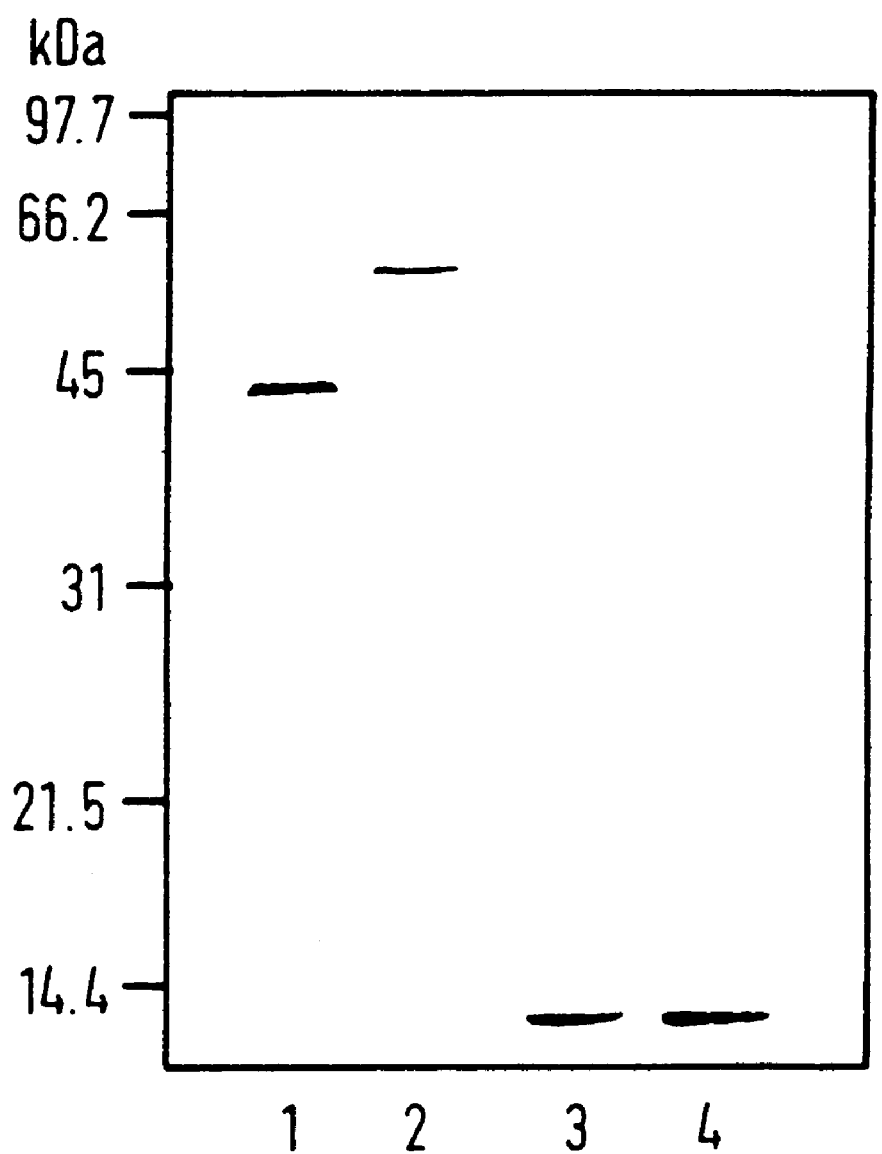

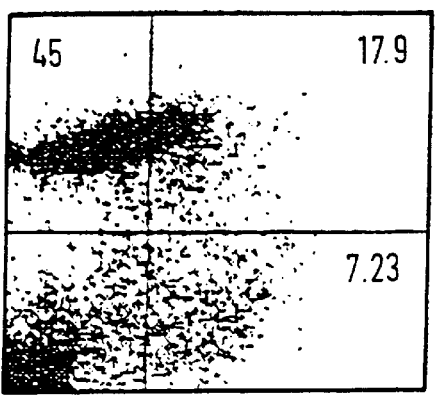
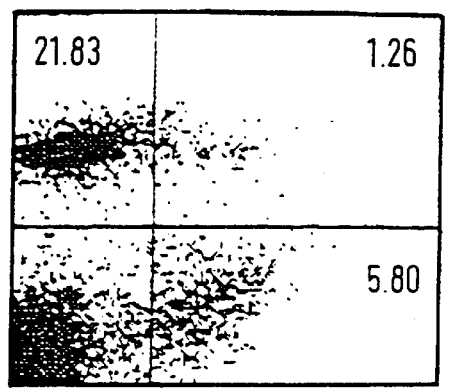
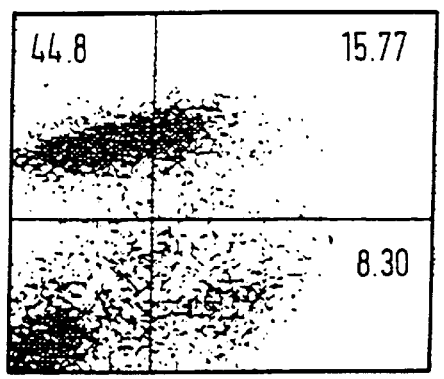
FIG. 4

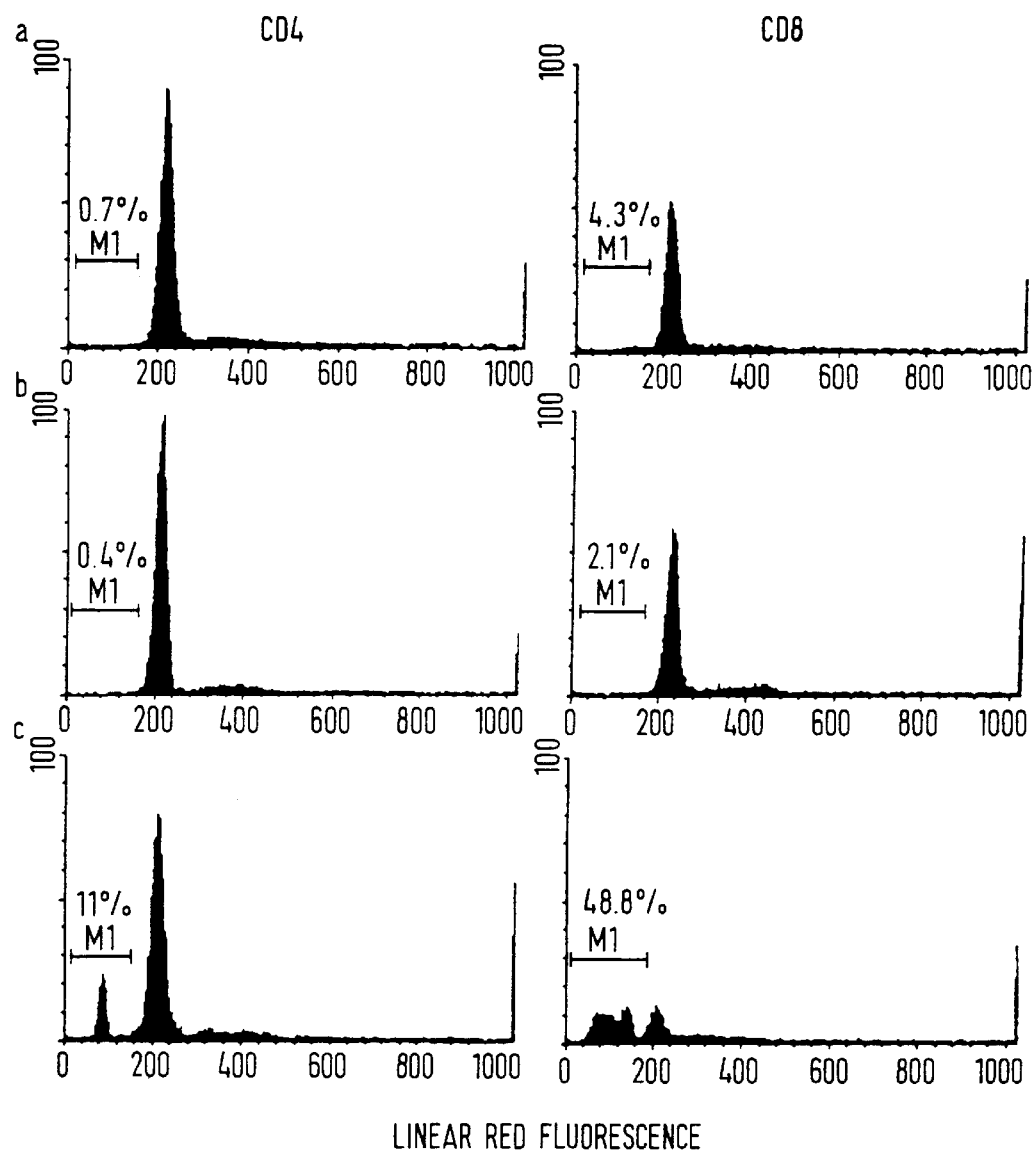

GM1-MEDIATED APOPTOSIS OF HUMAN PERIPHERAL BLOOD MONONUCLEAR CELLS

GM1-MEDIATED APOPTOSIS OF AN IMMORTALISED MURINE T-CELL LINE, CTLL

THERAPEUTIC AGENTS AND AUTOIMMUNE DISEASES

CROSS-REFERENCE TO RELATED APPLICATIONS

This application is a continuation of PCT application PCT/GB96/01614 filed Jul. 5, 1996.

BACKGROUND ART

This invention relates to therapeutic agents for use in the treatment of mammalian, particularly human, autoimmune diseases. The invention also relates to therapeutic agents useful in the treatment of human leukaemias of a T cell origin, as so-called "vaccine carriers", and as agents for use in the prevention of human transplantation rejection and graft versus host disease (GVHD).

In an article entitled "Morphologic and Functional Alterations of Mucosal T Cells by Cholera Toxin and its B subunit" by Charles O. Elson et al., The Journal of Immunology, 1995, 154; 1032–1040 it is disclosed that the cholera toxin (Ctx) and the CtxB subunit inhibit $CD8^+$ and $CD4^+$ T cells.

Reference is also made to the paper entitled "Prevention of Acute Graft-Versus-Host Disease by Treatment with a Novel Immunosuppressant" by B. Yankelevich et al., The Journal of Immunology, 1995, 154: 3611–3617. This identifies CtxB as an agent for use in bone marrow transplantation for the prevention of acute graft-versus-host disease (GVHD).

WO 95/10301 discloses an immunological tolerance-inducing agent comprising a mucosa-binding molecule linked to a specific tolerogen.

As used herein, the term "Ctx" refers to the cholera toxin and "CtxB" to the B subunit of the cholera toxin. In other texts, these may sometimes be identified as "CT" or "Ct" and "CTB" or "CtB" respectively. The term "Etx" herein means the E. coli heat labile enterotoxin, and "EtxB" is the B subunit of Etx. In other texts, these may sometimes be identified as "LT" or "Lt" and "LTB" or "LtB" respectively.

The basis for all aspects of the present invention is the finding that EtxB (the pure B-subunit of the E. coli heat labile enterotoxin) binds to GM1-ganglioside receptors which are found on the surfaces of mammalian cells, and that this binding induces differential effects on lymphocyte populations, including a specific depletion of $CD8^+$ T cells and an associated activation of B cells. These effects are absent when a mutant EtxB protein lacking GM1 binding activity is employed.

Autoimmune Disease

Autoimmunity is the term used to describe the mechanism by which the body generates an immune response to self-antigens.

SUMMARY OF THE INVENTION

In accordance with a first aspect of the invention, there is provided:

(i) an agent having GM-1 binding activity, other than Ctx or Etx, or the B subunits of Ctx and Etx; or (ii) an agent having an effect on GM-1 mediated intracellular signalling events, but no GM-1 binding activity;

for use as an agent in the treatment or the prevention of an autoimmune disease.

Agents in accordance with the present invention have been found to modulate lymphocyte populations leading to the induction of apoptosis in $CD8^+$ T cells, the enhanced activation of $CD4^+$ cells and polyclonal activation of B cells. These events are likely to shift the immune response towards induction of Th2 associated cytokines. Such responses to self or cross-reacting antigens are understood to mediate protection for certain autoimmune diseases.

In a first embodiment of this first aspect of the present invention, the agent is used in a method of treating an autoimmune disease which is in progress.

In this embodiment, the agent is administered to a patient with or without co-administration of a self or cross-reacting antigen. Administration of the agent in accordance with this embodiment of the first aspect of the invention modulates the nature of the immune response towards the self-antigen away from the activation of disease-causing inflammation and hence protects against autoimmune disease.

In a second embodiment of this first aspect of the present invention, the agent is used in a method for the "vaccination" of a mammalian subject against an autoimmune disease, in which the agent is co-administered with the self or cross-reacting antigenic determinant (or a combination of different self or cross-reacting antigenic determinants) associated with said disease. In such a manner, the subject's immune response to the self-antigen or cross-reacting antigen is switched away from the activation of pathogenesis, which therefore protects against a future autoimmune response to the self-antigen.

In this first aspect of the invention, the therapeutic agent and the self or cross-reacting antigenic determinant are, or may be, co-administered to the subject. By this we mean that the site and time of administration of each of the therapeutic agent and the antigenic determinant are such that the necessary modulation of the immune system is achieved. Thus, whilst the therapeutic agent and the antigenic determinant may be administered at the same moment in time and at the same site, there may be advantages in administering the therapeutic agent at a different time and to a different site from the antigenic determinant.

Whilst single doses of the therapeutic agent and the antigenic determinant may be satisfactory, multiple doses are contemplated within the scope of this aspect of the invention.

In this second embodiment of the first aspect of the invention, the therapeutic agent and the antigenic determinant may be linked, for example covalently linked, to form a single active agent, although separate administration, in which the therapeutic agent and the antigenic determinant are not so linked is preferred because it enables separate administration of the different moieties.

Specific autoimmune diseases which may be treated in accordance with this aspect of the present invention are the autoimmune diseases where pathology is associated with cell-mediated immunity, such as rheumatoid arthritis, multiple sclerosis and diabetes.

Additionally, under this first aspect of the present invention, there is provided the use of Ctx, Etx or the B subunit of Ctx or Etx, for the manufacture of a medicament for use as an agent for the prevention of an autoimmune disease.

Also provided is a pharmaceutical composition for the treatment of a human autoimmune disease comprising (i) an agent having GM-1 binding activity; or (ii) an agent having an effect on GM-1 mediated intracellular signalling events, but no GM-1 binding activity;

and a pharmaceutically acceptable carrier or di-luent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate self or cross-reacting antigen. Alternatively, a kit may be provided comprising separate compositions for each of the therapeutic agent and the antigenic determinant.

Specific therapeutic agents which may be used in this aspect of the invention are EtxB and CtxB or mutants thereof retaining GM1 binding activity.

The agents for use in the first aspect of the present invention should preferably be substantially non-toxic, although some degree of toxicity may be tolerated in a severe therapy of this kind.

This first aspect of the invention extends to cover the use of all agents having GM1 binding activity, for use in the treatment of mammalian autoimmune disease, as well as those agents having an effect on GM-1 mediated intracellular signalling events, and which therefore mimic GM-1 binding agents. Thus, this first aspect of the present invention is not limited to the use of EtxB protein as a therapeutic agent in the treatment of a human autoimmune disease. However, the use of the EtxB protein (which is a pentamer of five identical subunits) for such a treatment represents a preferred embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other therapeutic agents for the treatment of autoimmune disease in accordance with the first aspect of this invention are humanised monoclonal antibodies, which bind GM1. Methods known in the art for identifying and preparing such agents are well known.

T-lymphocyte Leukaemias

According to a second aspect of this invention, there is provided:
(i) an agent having GM-1 binding activity, other than Ctx or Etx, or the B subunits of Ctx and Etx; or
(ii) an agent having an effect on GM-1 mediated intracellular signalling events, but no GM-1 binding activity;
for use in the treatment of human leukaemias of a T cell origin, such as human leukaemias of a CD8 T cell origin.

The agents for use in the second aspect of the present invention should preferably be substantially non-toxic, although some degree of toxicity may be tolerated in a severe therapy of this kind.

Additionally, under this second aspect of the present invention, there is provided the use of Ctx or Etx, or the B subunits of Ctx and Etx for the manufacture of a medicament for treatment of human leukaemias of a T cell origin, such as human leukaemias of a CD8 T cell origin.

Also provided is a pharmaceutical composition for the treatment of human leukaemias of a T cell origin comprising
(i) an agent having GM-1 binding activity; or
(ii) an agent having an effect on GM-1 mediated intracellular signalling events, but no GM-1 binding activity;
and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

This second aspect of the invention extends to cover the use of all agents having GMI binding activity, for use in the treatment of human leukaemias of a T cell origin, as well as those agents having an effect on GM-1 mediated intracellular signalling events, and which therefore mimic GM-1 binding agents.

Thus, this second aspect of the present invention is not limited to the use of EtxB protein as therapeutic agents in the treatment of human T cell leukaemias. However, the use of the EtxB protein for such a treatment represents a preferred embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other alternative therapeutic agents for the treatment of these diseases in accordance with this aspect of the invention are humanised monoclonal antibodies, which bind GM1. Methods known in the art for identifying and preparing such agents are well known.

Transplant Relection and GVHD

In accordance with a third aspect of this invention, there is provided:
(i) an agent having GM-1 binding activity, other than Ctx or Etx, or the B subunits of Ctx and Etx; or
(ii) an agent having an effect on GM-1 mediated intracellular signalling events, but no GM-1 binding activity;
for use as a therapeutic agent for the prevention/treatment of transplant rejection or GVHD.

Additionally, under this third aspect of the present invention, there is provided the use of Ctx or Etx or the B subunit of Etx or Ctx for the manufacture of a medicament for the prevention of transplant rejection or GVHD.

In preferred embodiments of this aspect of the invention, the therapeutic agents described may be used in the prevention of solid organ transplant rejection, either allogeneic or xenogeneic. They may also be employed in the prevention of acute graft versus host disease (GVHD), for example during bone marrow transplantation procedure.

In embodiments of this aspect of the invention where the patient is treated prior to transplantation, the therapeutic agent would be co-administered with alloantigen or xenoantigen. In embodiments in which the patient is treated after transplantation, the therapeutic agent is employed without co-administration of antigen.

In the embodiment of this aspect of the invention, where the therapeutic agent and allo- or xeno-antigenic determinant are co-administered to the subject, we mean that the site and time of administration of each of the therapeutic agent and the antigenic determinant are such that the necessary modulation of the immune system is achieved. Thus, whilst the therapeutic agent and the antigenic determinant may be administered at the same moment in time and at the same site, there may be advantages in administering the therapeutic agent at a different time and to a different site from the antigenic determinant. Furthermore, the therapeutic agent and the antigenic determinant may be covalently linked to form a single active agent, although separate administration, in which the therapeutic agent and the antigenic determinant are not so linked is preferred because it enables separate administration of the different moieties.

Whilst single doses of the therapeutic agent and the antigenic determinant may be satisfactory, multiple doses are contemplated within the scope of this aspect of the invention.

In this aspect of the invention, where the agent is being used in the prevention of GVHD, the agent would normally be applied direct to the cells, for example bone marrow cells, to be transplanted.

The agent is preferably substantially non-toxic, although some degree of toxicity may be tolerated in severe therapies of this kind.

Also provided is a pharmaceutical composition for use in the treatment of transplant rejection, comprising (i) an agent having GM-1 binding activity; or (ii) an agent having an effect on GM-1 mediated intracellular signalling events, but no GM-1 binding activity;

and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate allo- or xeno-antigeneic determinant. Alternatively, a kit may be provided comprising separate compositions for each of the therapeutic agent and the antigenic determinant.

This third aspect of the invention extends to cover the use of all agents having GM1 binding activity, for use in the prevention/treatment of transplant rejection or GVHD, as well as those agents having an effect on GM-1 mediated intracellular signalling events, and which therefore mimic GM-1 binding agents.

Thus, this third aspect of the invention is not limited to the use of EtxB protein as a therapeutic agent in the treatment of a transplant rejection. However, the use of the EtxB protein (which is a pentamer of five identical subunits) for such a treatment represents a preferred embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other alternative therapeutic agents for the treatment of transplant rejection in accordance with the invention are humanised monoclonal antibodies, which bind GM1. Methods known in the art for identifying and preparing such agents are well known.

Vaccination

CtxB and EtxB have already been suggested as so-called "vaccine carriers". It has now been discovered that the basis for this effect, in part, is the ability of EtxB to modulate lymphocyte populations (as discussed above) by binding to the GM-1 receptor.

Thus, in accordance with a fourth aspect of the present invention, there is provided:

(i) an agent having GM-1 binding activity, other than Etx or Ctx or the B subunits of Etx or Ctx; or (ii) an agent having an effect on GM-1 mediated intracellular signalling events, but no GM-1 binding activity;

for use in the vaccination of a mammalian subject.

The agent is capable of modulating the immune response when delivered together with an unrelated foreign antigenic determinant. Where the agent is delivered parenterally, such immunomodulation is in terms of the immune response being "directed" in a particular desired direction. Where the agent is delivered mucosally with an unrelated antigen, as a so-called "mucosal adjuvant", the agent is capable of facilitating a mucosal immune response to the unrelated antigen. The antigen and agent may be delivered together as separate moieties, or may be linked together, for example by a covalent linkage.

The agent is preferably non-toxic. In addition, where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Also provided is a pharmaceutical composition for use in the vaccination of a mammalian subject, comprising (i) an agent having GM-1 binding activity; or (ii) an agent having an effect on GM-1 mediated intracellular signalling events, but no GM-1 binding activity;

and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate antigenic determinant. Alternatively, a kit may be provided comprising separate compositions for each of the therapeutic agent and the antigenic determinant.

This fourth aspect of the invention extends to cover the use of all agents having GM1 binding activity, as immunomodulators, as well as those agents having an effect on GM-1 mediated intracellular signalling events, and which therefore mimic GM-1 binding agents.

Thus, this fourth aspect of the invention is not limited to the use of EtxB protein as an immunomodulator. However, the use of the EtxB protein (which is a pentamer of five identical subunits) in such a way represents one embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other alternative therapeutic agents for use as an immunomodulator in accordance with this aspect of the invention are humanised monoclonal antibodies, which bind GM1. Methods known in the art for identifying and preparing such agents are well known.

When the therapeutic agent of the invention is a protein, such as the EtxB subunit or the CtxB subunit, it may be produced, for use in all aspects of this invention, by a method in which the gene or genes coding for the specific polypeptide chain (or chains) from which the protein is formed, is inserted into a suitable vector and then used to transfect a suitable host. For example, the gene coding for the polypeptide chain from which EtxB assemble may be inserted into, for example, plasmid pMMB68, which is then used to transfect host cells, such as Vibrio sp.60. The protein is purified and isolated in a manner known per se. Mutant genes expressing active mutant EtxB protein may then be produced by known methods from the wild type gene.

As previously stated, agents having GM-1 binding activity, such as specifically designed humanised monoclonal antibodies, may be designed and produced as outlined above, by methods which are known in the art.

In all aspects of the invention, the agent having GM1 binding activity may also be capable of cross-linking GM1 receptors. EtxB is one such agent which is capable of cross-linking GM1 receptors by virtue of its pentameric form.

The invention will now be illustrated by reference to the accompanying drawings and the following examples.

BRIEF DESCRIPTION OF THE DRAWINGS

FIG. 4 illustrates that EtxB causes increased activation of B cells;

FIG. 8 shows EtxB receptor-mediated apoptosis of $CD8^+$ T cells as measured by cell cycle analysis;

FIGS. 9*a* and 9*b* show the results of experiments conducted to show that GM-1 binding by EtxB inhibits the development of collagen induced arthritis in an animal model;

FIG. 10 shows the results of an experiment conducted to illustrate that EtxB but not EtxB(G33D) induces apoptosis in a population of normal human peripheral blood mononuclear cells; and FIG. 11 shows the results of an experiment which shows that cross-linking of GM1 leads to apoptosis in a proportion of murine CTLL cells.

DETAILED DESCRIPTION OF PREFERRED EMBODIMENTS

FIG. 1

Analysis of Physico-chemical Properties of EtxB and EtxB (G33D).

(A) SDS-PAGE analysis of EtxB or EtxB (G33D): 5 μg of each protein were analysed under reducing conditions in the presence of β-mercaptoethanol with or without prior heating. Lane 1, wild type EtxB, unheated. Lane 2, EtxB (G33D), unheated. Lane 3; wild type EtxB, heated at 95° C. Lane 4, EtxB (G33D), heated at 95° C. Molecular weight standards (BioRad) are shown on the left-hand side of the panel.

(B) Determination of apparent molecular mass of EtxB and EtxB (G33D) by gel filtration chromatography: standard curve (circles) was generated using, from top to bottom: bovine serum albumin (66 kDa), hen egg albumin (45 kDa), bovine erythrocyte carbonic anhydrase (29 kDa) and horse heart cytochrome c (12.4 kDa); EtxB and EtxB (G33D) eluted with apparent molecular masses of 36 kDa and 38 kDa respectively; Ve-elution volume of the protein, Vo-void volume of the gel filtration column.

(C) ELISA for comparative binding of EtxB and EtxB (G33D) to ganglioside GM1: plates were coated with GM1, blocked and incubated with 1 μg/ml of either EtxB or EtxB (G33D) diluted serially (3 fold) from 1 μg/ml.

FIG. 2

Receptor Binding by EtxB is Essential for its Potent Immunogenicity in vivo.

BALB/c mice (4 in each group) were either injected s.c. with EtxB or EtxB (G33D) in PBS or given the proteins orally in bicarbonate buffer. Sera were analysed 10 days following two s.c. injections (A) or 1 week following 3 oral doses (B), and gut secretions were analysed 1 week following 3 oral doses (C). No reaction was detected in samples from control mice (not shown). Results are expressed as mean IgG antibody titre in serum, while IgA in gut secretion is expressed as 'specific activity' as described below.

FIG. 3

Kinetics of Lymphocyte Proliferation.

Mice were injected i.p. with 30 μg of EtxB (G33D) in complete Freund's adjuvant. MLNs were isolated 10 days later and cells were incubated in the absence of antigen (open square) or in the presence of 80 μg/ml EtxB (filled triangles), EtxB (G33D) (open triangles) or their disassembled monomeric forms of EtxB (filled circles) and EtxB (G33D) (open circles) generated by heating at 95° C. The last 6 hour on each sampling day cells were pulsed with 1 μCi of ($^3$H) Thd. Data represents mean cpm and SEM of triplicate wells.

FIG. 4

EtxB Causes Increased Activation of B Cells.

Mice were immunized with EtxB (G33D) in CFA. Cells were isolated from MLN 10 days later and incubated in the presence of 80 μg/ml of either EtxB or EtxB (G33D) or a mixture of 40 μg/ml of each protein. Cells were labelled with biotinylated anti-CD25 (7D4) and Phycoerythrin (PE) anti-B220 (Ra3-6D2). Streptavidin FITC was used as a secondary antibody conjugate. Controls for the antibodies were also included (not shown). Dual flow cytometric analysis was performed on day 4 of proliferation.

FIG. 5

EtxB Causes Increased Activation of CD4+ T Cells and Depletion of CD8*T Cells.

The immunization procedure, cell isolation and the in vitro challenge are as described in the legend of FIG. 4. To detect CD25, biotinylated anti-CD25 (7D4) and Streptavidin FITC were used. To detect CD4 and CD8, FITC labelled anti-CD4 (RNRM4-5) and FITC labelled anti-CD8α (53-6.7) were used. Appropriate controls for the antibodies were included (not shown).

FIG. 6

Selective Depletion of OVA-responsive $CD8^+$ T Cells by EtxB.

Cultures of cells from MLN taken from OVA-primed mice were established for 5 days, in the absence of antigen or in the presence of OVA+EtxB, OVA+EtxB(G33D) or OVA alone at 100 μg OVA and 40 μg/ml each of EtxB or EtxB(G33D) or 100 μg OVA alone. Cells were labelled with the following rat antibodies: FITC-anti-CD4 or FITC-anti-CD8α and both with biotin-anti-CD25 (IL-2Rα) followed by Streptavidin-phycoerythrin. Non-stained cells or cells stained with the second antibody alone were also included as controls. Cells were analysed by FACS (Becton Dickinson). The higher increase in the proportion of total cells which are CD25+ in cultures containing EtxB compared with other treatments is due to the presence of higher proportion of B cells expressing this marker (not shown). The scale of fluorescence intensity is log.

FIG. 7

Receptor Binding by EtxB Induces Alterations in Lymphocyte Nuclear Morphology Characteristic of Cells Undergoing Apoptosis.

MLNC comprising >90% $CD3^+$ T cells and depleted of macrophages were incubated for 18 h with either 80 μg/ml EtxB or with 80 μg/ml EtxB(G33D) and stained with acridine orange. Cells were examined under conventional or confocal fluorescence microscopy (Leica TCS 4D). A representative microscopic field (×540) for each treatment is shown [EtxB, left hand panel; EtxB (G33D), right hand panel]. Cells which were incubated in the absence of antigen gave similar results to those treated with EtxB(G33D) (not shown).

FIG. 8

EtxB Receptor-mediated Apoptosis of CD8$^+$ T cells as Measured by Cell Cycle Analysis.

Figure 7:
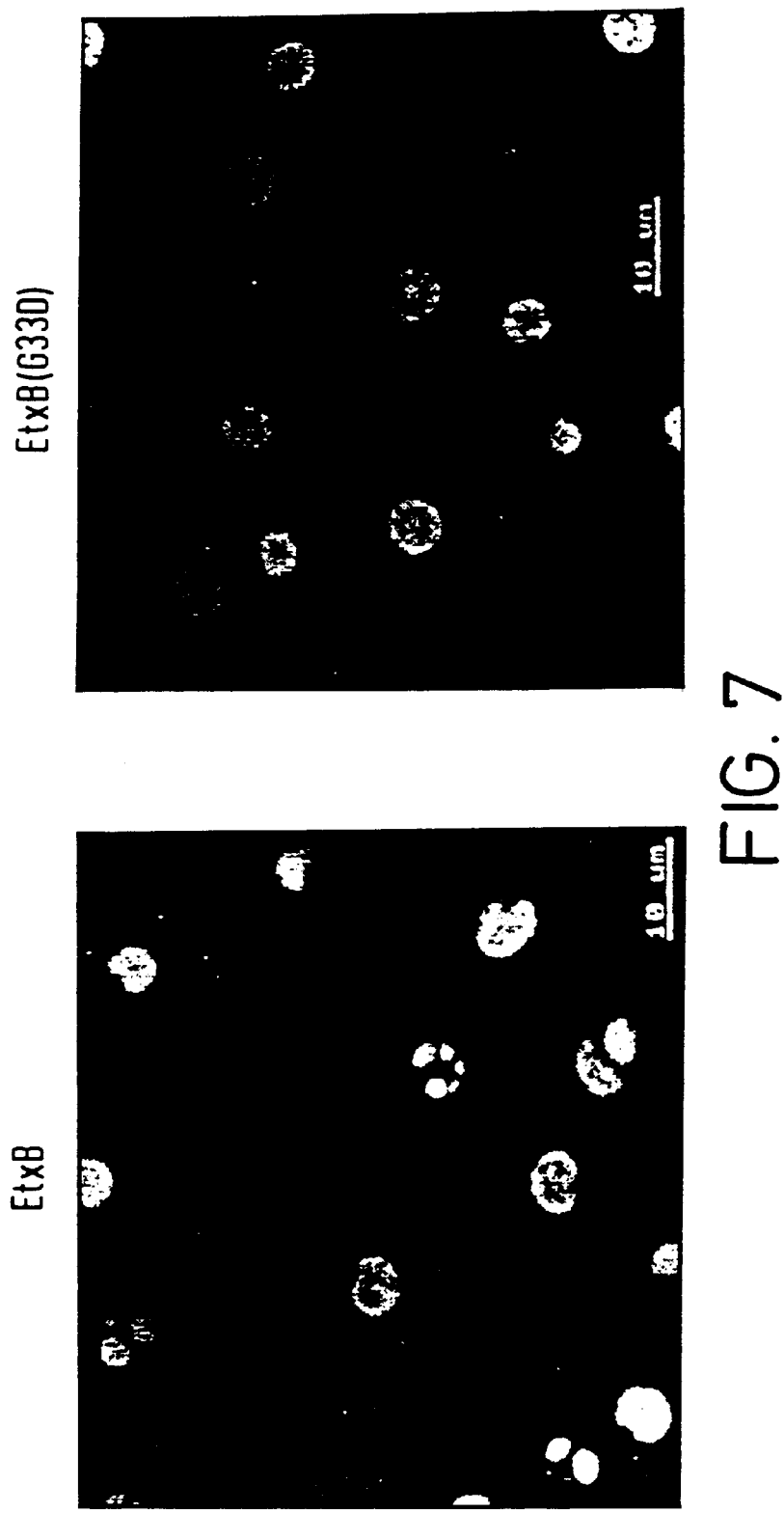
FIG. 7 shows that receptor binding by EtxB induces alterations in lymphocyte nuclear morphology characteristic of cells undergoing apoptosis.
Figure 9B:
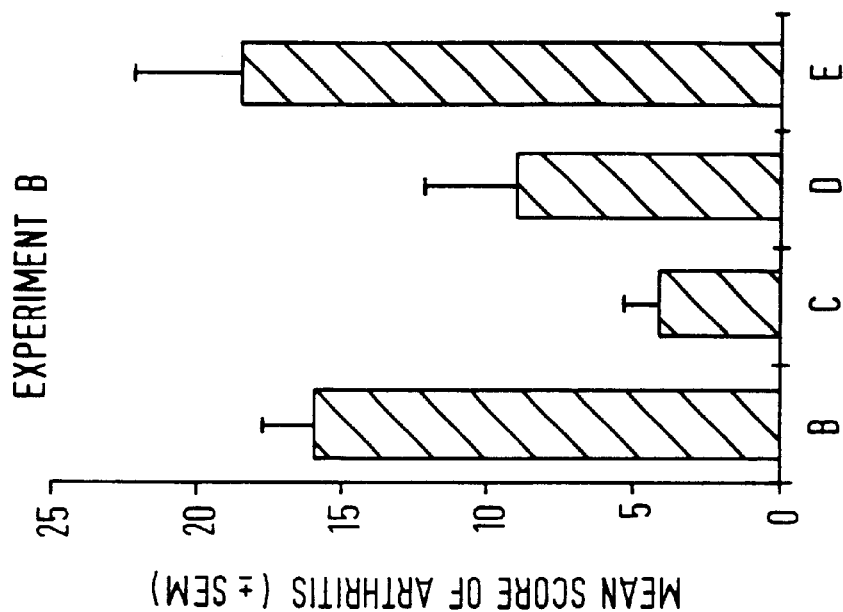
Figure 9A:
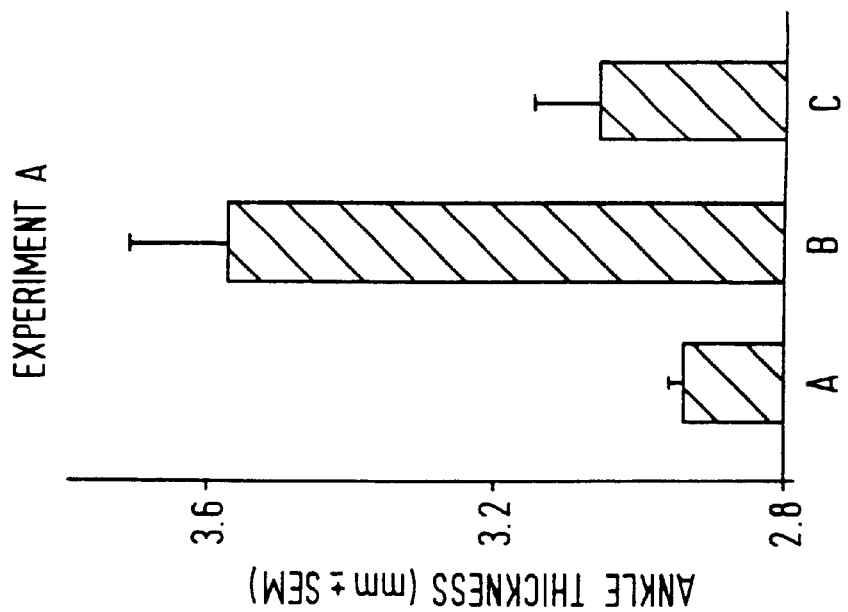
Figure 10:
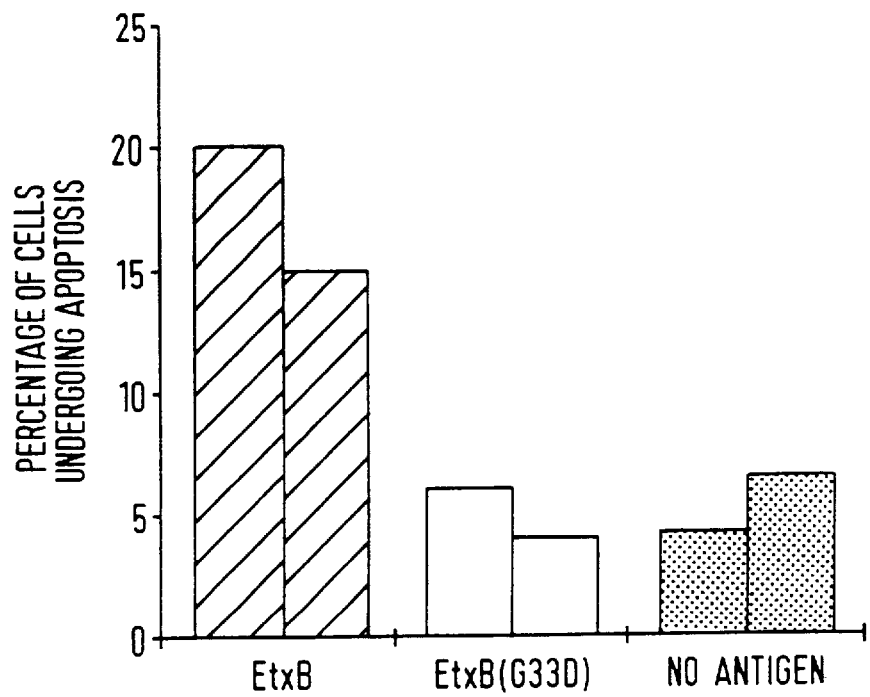
Figure 11:
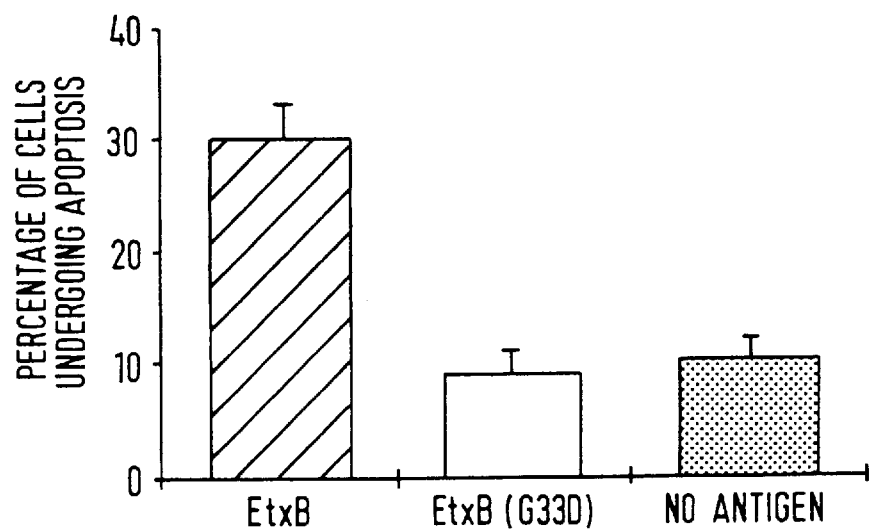

The proportion of CD4$^+$ and CD8$^+$ SPLTC in the sub-$G_0$/$G_1$ stage of the cell cycle was determined by flow cytometric analysis of the DNA content following staining with propidium iodide. SPLTC were isolated from the spleen by negative selection as described above. The cells were treated for 18 h with: (a) no antigen, (b) 80 μg/ml EtxB(G33D) or (c) 80 μg/ml EtxB and then stained with FITC-rat anti-CD4 or FITC-rat anti-CD8α. The cells were subsequently stained with propidium iodide. The proportion of cells co-stained with propidium iodide was determined by gating on cells stained with either anti-CD4 or anti-CD8 antibodies. This experiment has been carried out on cells, results of which are also reported in FIG. 7 and Table 3.

EXAMPLES

Example 1

This example illustrates the requirement for GM-1 binding to induce differential effects on lymphocyte populations.

Materials and Methods
Generation of a Receptor-binding Mutant of EtxB

A Gly-33 to Asp substitution was introduced into the receptor binding site of human EtxB using plasmid pTRH29, a derivative of the phagemid vector pBluescript IIKS+, that contains the genes for the A- and B-subunits of Etx (Yu, J., Webb, H. & Hirst, T. R. (1992), Molec. Microbiol. 6, 1949–1958). Mutagenesis was performed with an in vitro oligonucleotide-directed mutagenesis kit (Amersham International) using single-stranded pTRH29 as a template and a synthetic oligonucleotide (5'-TCTCTTTTATCTGCCATCG-3') (from the Microanalytical Facility, IAPGR, Cambridge Research Station, UK) as the mutagenic primer. The correct Gly to Asp substitution was confirmed by dideoxy sequencing using Sequenase II (United States Biochemical Corp.) and the resultant plasmid was designated pTRH56. The mutant etxB gene from pTRH56 was excised, using EcoRI and SpeI restriction enzymes, and inserted into pMMB68 (Sandkvist, M., Hirst, T. R. & Bagdasarian, M. (1987) J. Bacteriol. 169, 4570–4576) to yield a broad host range expression vector, pTRH64 expressing EtxB(G33D).

Antigens

Wild-type EtxB and EtxB(G33D) were purified from culture supernatants of Vibrio sp.60 (pMMB68) and Vibrio sp.60 (pTRH64), respectively, using a modification of the method reported by Amin and Hirst (Amin, T., & Hirst, T. R. (1994) Prot. Express. and Purif. 5, 198–204). Briefly, proteins were purified by diafiltration and hydrophobic interaction chromatography and concentrated by anion-exchange chromatography. The protein solutions were desalted on a PD10 column (Pharmacia, UK) equilibrated with phosphate buffered saline (PBS; 10 mM sodium phosphate, 150 mM NaCl, pH7.4) and stored at −30° C.

The purity of EtxB and EtxB(G33D) were confirmed by SDS polyacrylamide gel electrophoresis. The molecular mass of the individual monomers were confirmed by laser desorption mass spectrometry (Protein Science Facility, University of Kent).

Apparent molecular masses of EtxB and EtxB(G33D) were determined by gel filtration chromatography using a SMART system (Pharmacia). Proteins were eluted from a Superdex 75 PC 3.2/30 column in PBS, pH7.5.

Irreversible denaturation of B subunit pentamers, for use in lymphocyte proliferation assays (see below), was achieved by heating the proteins at 95° C. for 5 min.

Animals, Sample Collection and Immunization Protocols

BALB/c mice (H-2$^d$; high responder to EtxB) of 7–12 weeks of age were purchased from Charles River Laboratories and maintained at the University of Kent animal house. Antibody responses to EtxB or EtxB(G33D) were measured after s.c. injection of mice with 30 μg of protein in PBS, followed by boosting 10 days later. Another group of mice were given the same protein dose orally in sodium bicarbonate (50 μg/ml) on 3 occasions, and at one week intervals. Control mice were given PBS. Blood was collected 10 days following the last s.c. injection or one week following the last oral feeding. Gut secretions from live mice were isolated in a protease inhibitor solution as previously described (Elson, C. O., Ealding, W. & Lefkowitz, J. (1984) J Immunol. Meth. 67, 101–108), one week following the last feeding. Samples were then sonicated and clarified by centrifugation (13,226×g, min, at 4° C.).

For the proliferative assays, mice were injected i.p. with 30 μg of EtxB or EtxB(G33D) in complete Freund's adjuvant (CFA) and the mesenteric lymph nodes isolated 10 days later. Control unimmunized mice were also included and their lymph nodes isolated in a similar manner.

Enzyme Linked Immunosorbent Assays (ELISAs)

Binding of EtxB or EtxB(G33D) to GM1 was examined by a GM1-ELISA (Amin, T., & Hirst, T. R. (1994) Prot. Express. and Purif. 5, 198–204).

Sera and gut secretions were examined for the presence of anti-B subunit IgG and IgA antibodies by ELISA's in which samples were applied to microtitre plates (Immulon I, Dynateck, USA) coated with 5 μg/ml of either EtxB or EtxB (G33D) in PBS. Anti-B subunits IgA antibodies in gut secretion supernatants were extrapolated from a standard curve made by coating 2 rows of wells on each plate with 1 μg/ml rabbit anti-mouse IgA (α chain specific; Zymed Lab, USA) in PBS followed by addition of 1 μg/ml of mouse myeloma IgA (MOPC 315, Sigma, USA). To measure total IgA, wells were coated with rabbit anti-mouse IgA followed by addition of gut secretion supernatants. All samples were serially diluted. Goat anti-mouse IgG (Fc fragment specific; Jackson Lab., USA) or goat anti-mouse IgA (a chain specific; Sigma) peroxidase conjugate were diluted and added to all wells. The anti-B subunit IgG titer, giving an $A_{450nm} \geq 0.2$, was determined. The IgA anti-B subunit response for each of EtxB and EtxB (G33D) in gut secretions was calculated as "IgA specific activity" [mean IgA anti-B subunit (μg/ml)/total IgA (μg/ml)].

An ELISA method for measuring cytokine levels of IL-2, IL-4, IL-5, IL-10 and IFN-γ was used, as described previously (Harper, H. M., PhD thesis, Univeristy of Bristol (1995)). Briefly, microtiter plates were coated with rat antibodies to mouse IL-2, IL-4, IL-5, IL-10 and IFN-γ. Plates were blocked with 2% (w/v) bovine serum albumin. Supernatants from culture medium were added to wells and diluted down. One row on each plate for each cytokine contained a standard amount of recombinant cytokines. Plates were then incubated with 0.5 μg/ml of biotinylated anti-cytokine monoclonal antibodies followed by addition of avidine-peroxidase and 3,3',5,5'-Tetramethylbenzidene (TMB) substrate and read at $A_{405nm}$.

Lymphocyte Proliferation Assay

Mice were sacrificed by cervical dislocation, mesenteric lymph nodes were excised aseptically and minced through a stainless steel mesh into Hank's balanced salt solution (HBSS) (Flow Laboratories, Irvine, Renfrewshire, UK.). Cells were washed by centrifugation (500×g, 10 min, 4° C.) in HBSS and resuspended in modified Eagle's medium (Flow) to which 20 mM Hepes (Flow), 100 IU Penicillin, 100 μg/ml Streptomycin, 4 mM L-glutamine (Flow) and 2-mercaptoethanol had been added (complete medium). Fresh autologous normal mouse serum from unimmunized mice was added to a final concentration of 0.5% (v/v). Cultures contained $2\times10^6$ viable cells/ml in either 2 ml volumes in 24-well plates or 8 ml volumes in 25 $cm^3$ flasks (Nunc A/S, Roskide, Denmark) and were established in the presence and absence of antigens as indicated in the figures legend. Cultures were incubated at 37° C. in a humidified atmosphere of 5% $CO_2$ and 95% air for 6 days. At desired timepoints, 0.1 ml samples were removed from the cultures and transferred to 96 well U-bottomed plates (Nunc) and pulsed with 1 μCi/well of [$^3$H]-Thd (Amersham, U.K) for 6 h before harvesting (Mach III harvesting 96 Tomtec, Orange, Conn. USA) and counting by standard liquid scintillation 1450 Micro β plus, LKB-Wallac, Turku, Finland). Similarly, 0.5 ml of supernatant was sampled from cultures for cytokine analysis. Cells were pelleted and the supernatants stored at −68° C. until analysed.

Phenotypic Analysis of Cultured Cells

Cultured cells harvested on day 4 of culture were washed and viable cells recovered at the interface of a HBSS/18% metrizamide (Nyegaard and Co., Oslo, Norway) gradient following centrifugation at 500×g for 15 min at 20° C. Cells were washed twice and resuspended in HBSS containing 0.2% sodium azide (Sigma) and 10% normal rat serum. The following rat antibodies (Pharmingen, San Diego, USA) were used: fluorescein isothiocyanate (FITC) labelled anti-CD4 (RNRM4-5), FITC labelled anti-CD8 (53-6.7), biotin-labelled anti-CD25 (7D4) and Phycoerythrin (PE) labelled anti-B220 (RA3-6D2). Additionally, for the biotin-labelled antibodies Streptavidin-PE or Streptavidin-FITC (Serotech, UK) were used. All antibodies were diluted in HBSS containing azide and used at predetermined concentrations. 200 μl of $2\times10^6$ cells and 200 μl of each the antibodies were mixed and incubated on ice for 30 min. When Streptavidin-PE or FITC secondary antibodies were required cells were incubated with these antibodies for additional 30 min. Appropriate controls for FITC and PE antibodies were also included. Cells were washed with HBSS and then analysed by 2 flow cytometery (Becton Dickinson).

Results

Generation and Characterization of a Receptor Binding Mutant of EtxB

A Gly to Asp substitution was introduced into the B subunit of *E. coli* heat-labile enterotoxin by oligonulceotide-directed mutagenesis of EtxB, in order to generate a mutant B subunit defective in receptor recognition. The mutant protein, designated EtxB(G33D), and wild type EtxB were purified to homogeneity (see Materials and Methods). The molecular mass of purified EtxB and EtxB(G33D) were determined by laser desorption mass spectrometry. Masses were within 20 Da of the theoretical masses of 11702 and 11760 Da for monomeric EtxB and EtxB (G33D), respectively. When analysed by SDS-PAGE without prior heating, both wild-type EtxB and EtxB(G33D) migrated as discrete stable oligomers, with apparent molecular weights of 42 kDa and 56 kDa (FIG. 1A, lane 1 and lane 2, respectively). The observed electrophoretic mobility and SDS-stability of EtxB is a characteristic property of the B subunit pentamer (see Sandkvist, M., Hirst, T. R. & Bagdasarian, M. (1987) J. Bacteriol. 169, 4570–4576). The slower electrophoretic mobility of oligomeric EtxB(G33D) is not due to a difference in the number of constituent B subunit monomers, since both pentameric EtxB and EtxB(G33D) exhibited similar retention times when analysed by high resolution gel filtration chromatography. Thus, the discrepancy in the electrophoretic mobility of the EtxB(G33D) oligomer with respect to wild-type EtxB, is likely to be due to the introduced negatively charged Asp residue causing a reduction in SDS binding and a subsequent slower migration.

EtxB and EtxB(G33D) were also compared for their stability in low pH buffers, resistance to 1.0 mg/ml of either trypsin or proteinase K, and relative reactivity towards a panel of anti-B subunit monoclonal and polyclonal antibodies. In each of these tests EtxB(G33D) exhibited identical properties to wild-type EtxB. It is therefore concluded that a Gly to Asp substitution at residue 33. in EtxB does not alter the oligomeric configuration, SDS, pH or protease stability, or antibody reactivity compared with wild-type EtxB.

The ability of EtxB(G33D) to bind to its receptor GM1, was evaluated using a GM1-ELISA (FIG. 1C). This showed a highly significant reduction in the ability of the mutant to bind GM1 compared with the wild type protein (>99% reduction in the $A_{450nm}$ reading). Furthermore, in contrast to wild type EtxB, EtxB(G33D) failed to bind to CHO cells when examined by immunofluorescence. It is concluded that EtxB(G33D) is defective in its capacity to bind GM1 ganglioside, in vitro and in situ.

The Potent Immunogenicity of EtxB in vivo is Dependent on Receptor Binding

The importance of receptor binding in the immunogenicity of EtxB was evaluated in mice following either oral delivery or s.c. injection of EtxB or EtxB(G33D) in PBS. Oral delivery of EtxB resulted in detection of a high IgG antibody titer in serum and IgA antibody activity in gut secretions (FIG. 2). In contrast, a similar regime of oral immunization with EtxB(G33D) failed to generate any detectable antibody activity. EtxB(G33D) did induce a serum antibody response following s.c. injection, although the response was considerably lower in comparison to the antibody response to wild type EtxB, with >160 fold reduction in the mean antibody titer, 1050 versus 171000, respectively. It is concluded that receptor binding by EtxB is essential for its potent immunogenicity in vivo.

Receptor Binding does not Influence the Extent of Lymphocyte Proliferation in the Presence of EtxB or EtxB(G33D)

The effect of EtxB or EtxB(G33D) on lymphocyte proliferation in vitro was examined. Lymphocytes were isolated from the popliteal and mesenteric lymph nodes (MLN) of mice immunized with either EtxB or EtxB(G33D) and stimulated in vitro with either protein, or with a heat-denatured preparation of EtxB or EtxB(G33D). The proliferative response of lymphocytes derived from the popliteal or MLN was similar. In each case, proliferation to each of the protein preparations increased with increasing B subunit concentration. A representative set of data from an experiment using MLN is shown in Table 1. The magnitude of the response to wild type and mutant pentamers was comparable as was that in the presence of heat-denatured wild type and mutant monomers. FIG. 3 shows the kinetics of the proliferative responses obtained in the presence of 80 μg/ml of each of the protein preparations. Reactivity was dependent on the presence of antigen, and followed a similar pattern in the presence of each protein. Reactivity was evident on day 3 of culture with incorporation of [$^3$H]-Thd reaching a peak on day 4 and waining thereafter. The minor differences in the timing of peak responses apparent in FIG. 3 were not observed in repeat experiments, showing that the anamnestic characteristics of the responses to the EtxB and EtxB(G33D) are comparable. It is concluded that the level of stimulation in the presence of the native proteins is not likely to be influenced by receptor binding or the introduced mutation.

Toxin Receptor Binding Causes Immunomodulation of B Cells and T Cell Subsets To examine if receptor binding by EtxB exerts any effect on the populations of lymphoid cells in vitro, lymphocytes were isolated from the MLN of mice primed i.p. with EtxB(G33D) and then stimulated with either EtxB or EtxB (G33D) or a mixture of both. Additionally, a parallel experiment using MLN-derived lymphocytes from mice injected with EtxB was undertaken and resulted in essentially identical findings to those obtained from EtxB(G33D) primed mice.

(i) EtxB Causes Increased Activation of B Cells

The effect of EtxB on B cells were examined by expression of the activation marker CD25 (IL-2R$\alpha$) in association with the B cell marker B220 (CD45R). As shown in FIG. 4 the number of B cells in cultures stimulated with EtxB was 62.9% of total cells, of which a high proportion (28.4%) expressed the cell activation marker CD25. In contrast, the proportion of B cells after stimulation in the presence of EtxB(G33D) was less than half of that of the wild type (22.26%) and fewer were activated (5.6%). To establish whether the effects exerted by EtxB were dominant, cells were incubated in the presence of an equimolar concentration of EtxB and EtxB(G33D). The flow cytometric data was similar to that obtained following stimulation in the presence of wild type EtxB alone (with 60.6% B cells, of which 26% were activated). It is concluded that the receptor binding property of EtxB mediates an increased activation of B cells in vitro.

(ii) EtxB Causes Increased Activation of CD4$^+$ T Cells and Complete Depletion of CD8$^+$ T Cells.

Figure 1B:
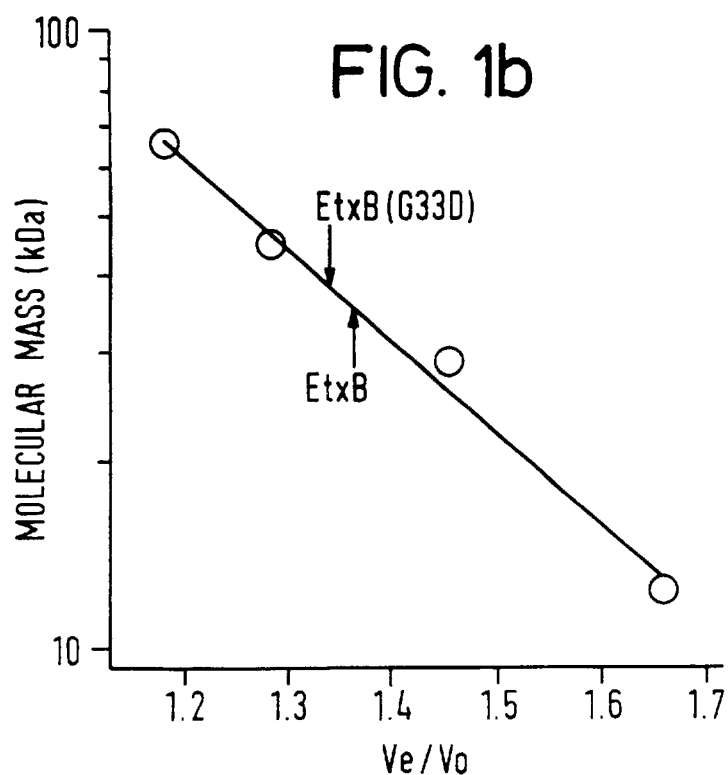
FIG. 1 represents an analysis of physico-chemical properties of EtxB and a mutant form of EtxB, (EtxB(G33D))
Figure 1C:
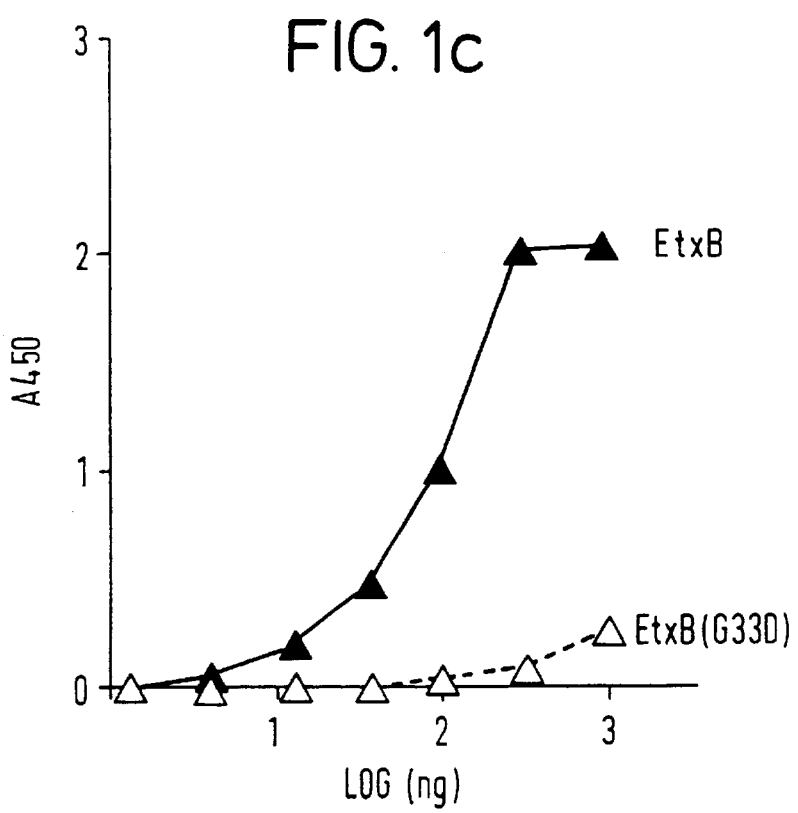
Figure 2:
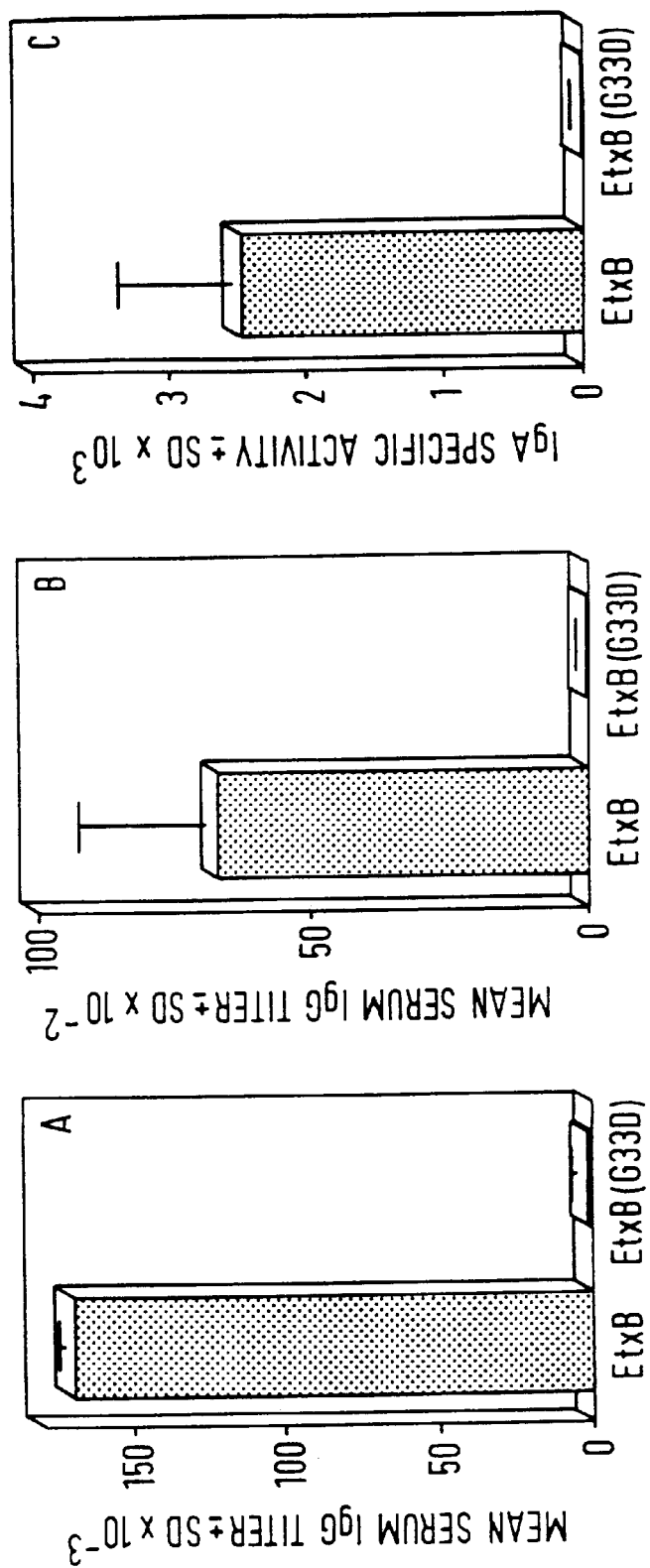
FIG. 2 illustrates that receptor binding by EtxB is essential for its potent immunogenicity in vivo.
Figure 3:
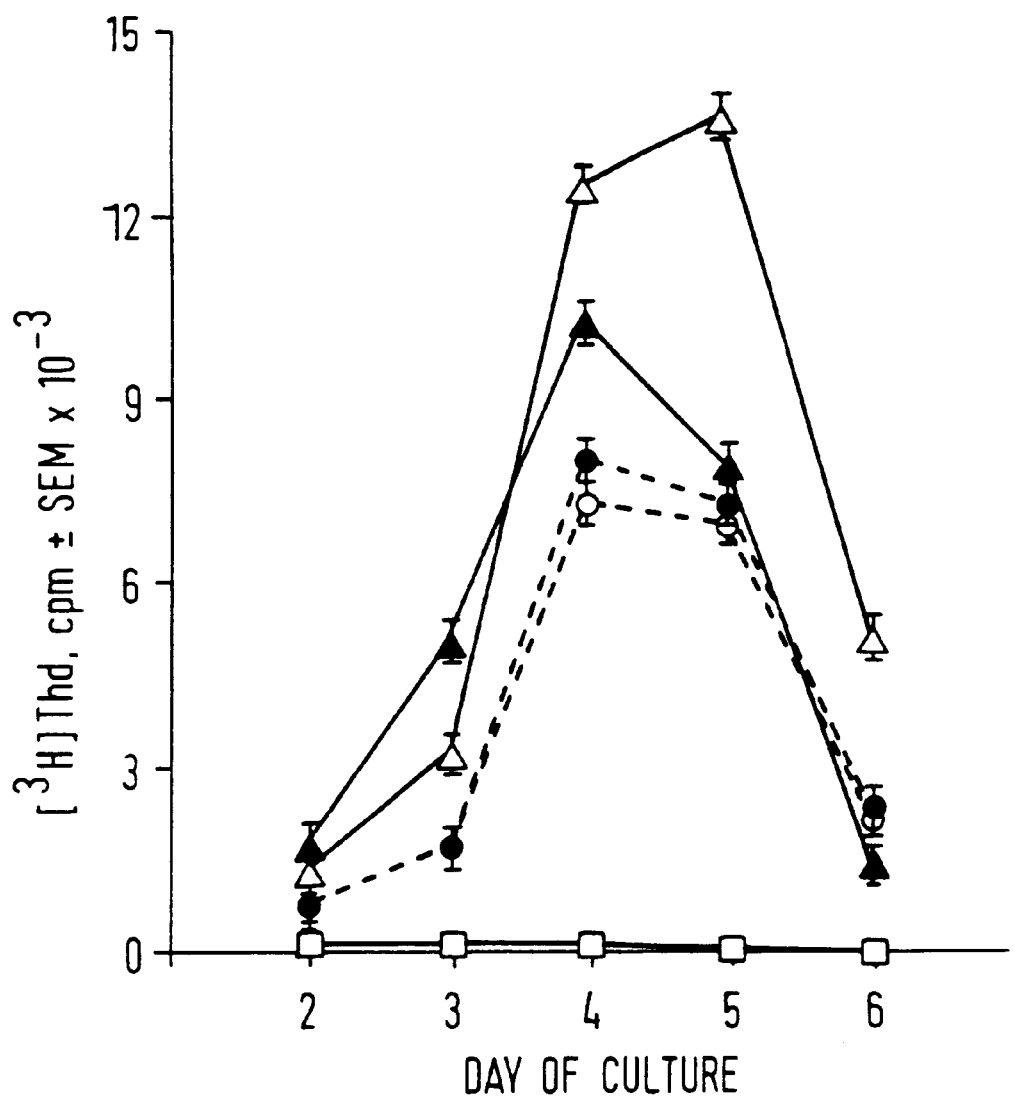
FIG. 3 illustrates the kinetics of lymphocyte proliferation following injection of mice with EtxB.
Figure 5:
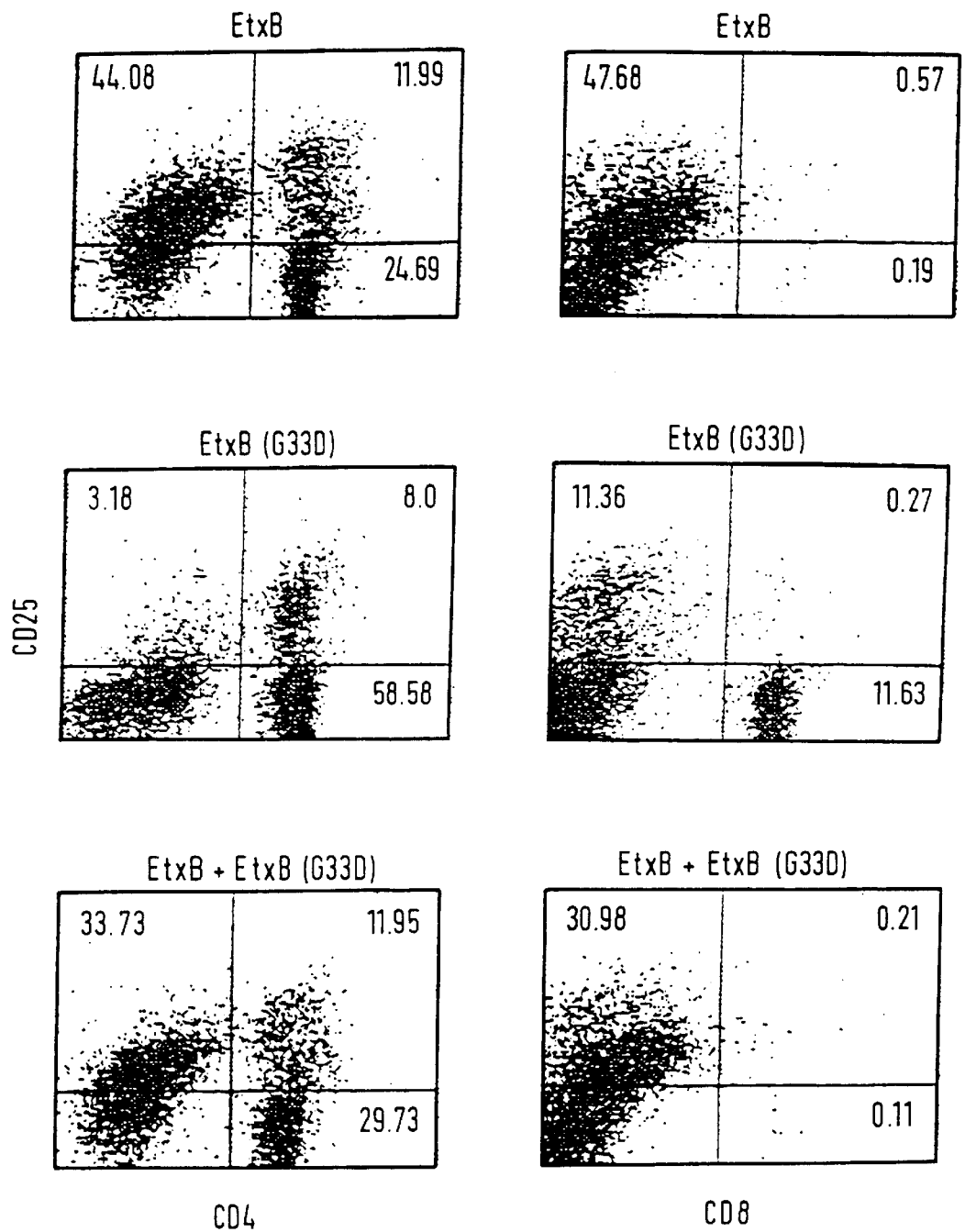
FIG. 5 illustrates that EtxB causes increased activation of $CD4^+$ T cells and depletion of $CD8^+$ cells.

To examine the influence of B subunit receptor binding on T cells, lymphocytes were labelled with antibodies to CD4 or to CD8 in association with antibodies to CD25 (FIG. 5). Additionally, some cells were separately labelled with antibodies to the CD3 marker (not shown). The proportion of T cells expressing the CD4 marker when stimulated in the presence of EtxB was 36.7%, of which a high proportion (32.7%) were activated. In contrast, no detectable CD8$^+$ T cells were present in the culture containing EtxB.

By comparison, both CD4$^+$ and CD8$^+$ T cells were present in the culture stimulated in the presence of EtxB(G33D). Such cultures contained a large proportion of CD4$^+$ T cells (66.6%), but only 12% of these were activated. The proportion of CD8$^+$ T cells detected in the presence of EtxB(G33D) was 11.7% of the total number of cells, but very few of these were activated which is indicated by the absence of the CD25 marker. Additionally, in the presence of a mixture consisting of an equimolar concentration of EtxB and EtxB (G33D) the pattern of responding cells was similar to that in the presence of wild type EtxB alone; with 41.68% CD4$^+$ T cells (of which 28.6% were CD25+) and no detectable CD8$^+$ T cells (FIG. 5). In all these analyses, the proportion of cells staining with CD3 was approximately equal to the sum of those expressing CD4 and CD8 markers. These data demonstrate that the increase in activation of B and CD4$^+$ T cells and the selective depletion of CD8$^+$ T cells are mediated by toxin receptor occupancy.

Production of Cytokines

To assess whether the effect of EtxB on lymphocyte populations could be dependent on a change in cytokine production, cell cultures were incubated with either EtxB or EtxB(G33D) and supernatants removed on days 2, 3, 4, 5 and 6 for analysis. The results from samples collected on day 5 are shown in Table 2 when the maximum concentration of cytokines was detected. Both IFN-$\gamma$ and IL-2 were detected in the supernatants from cultures stimulated in the presence of EtxB or EtxB(G33D), although the relative levels of these cytokines varied. The medium from cells incubated with wild type EtxB, contained a 3-fold higher concentration of IL-2 and a 1.5 fold lower level of IFN-$\gamma$ compared with supernatants from cultures stimulated in the presence of EtxB(G33D). Despite the finding that other proliferating T cell cultures responding to other antigens yielded high levels of IL-4, IL-5 and IL-10 none of these cytokines were detected in cultures stimulated with EtxB or EtxB(G33D). The increase in the level of IL-2 and decrease in the level of IFN-$\gamma$ following stimulation with EtxB, compared with EtxB(G33D), most likely reflects the activation status of B and CD4$^+$ T cells. Nonetheless, the results indicate that the profound effect of wild type EtxB on the CD8$^+$ T cell population is unlikely to be mediated by a major shift in the cytokine profile, as a consequence of receptor occupancy.

DISCUSSION

These investigations show that the introduction of a single point mutation (G33D) in the receptor binding site of EtxB caused a significant loss in the ability to bind GM1. Importantly, the mutant EtxB(G33D), exhibited identical physico-chemical properties to the wild type EtxB with respect to conformation, as revealed by gel chromatography, stability in SDS, acid and proteases. When the specific antibody responses were measured following immunization with either EtxB or EtxB(G33D), dramatic differences were noted. Subcutaneous injection with EtxB(G33D) in mice resulted in a highly significant drop in the antibody titer compared with wild type (ca>160 folds) while no antibody response was detected following oral administration. It is possible that these differences result from the disruption of a dominant epitope involved either in the recognition of the molecule by antibody, or the stimulation of effective T cell help for antibody production. However, it is noteworthy that the Gly to Asp substitution had no effect on the recognition of the B subunit by a panel of specific polyclonal and monoclonal antibodies. Further, the proliferative responses obtained when EtxB or EtxB(G33D) were added to cultures were comparable regardless of which of the proteins were used for in vivo priming; demonstrating that the T cell reactivity was not specific to either molecule. It is therefore concluded that receptor binding by EtxB is essential for its potent immunogenicity in vivo.

The importance of receptor binding in the potent immunogenicity of EtxB may be explained in a number of ways. Firstly, binding of the B subunit of Etx and Ctx to GM1 may increase the efficiency of uptake of these proteins, raising the local protein concentration available to the immune system. Other classes of proteins which are able to bind mucosal surfaces are found to be effective immunogens (De Aizpura, H. J. & Russell-Jones, G. J. (1988) J. Exp. Med. 167, 440–451). The observed differences in the immunogenicity of EtxB and its mutant following oral administration may indeed be due to efficient uptake of EtxB from the lumen of the gut. However, the dramatic differences noted after parenteral immunization (where antigen is delivered locally at high concentration) are suggestive of other effects. For example, binding of EtxB to GM1 may affect the efficiency of antigen presenting cell activity. Such binding could cause activation of class II-bearing cells, particularly with respect to their expression of essential co-stimulatory molecules, such as B7, which is associated with their acquiring enhanced antigen presenting activity (Jenkins, M. K. & Johnson, J. G. (1993) Curr. Opin. Immunol. 5, 361–367). Alteratively, receptor binding may have direct effects on sub-populations of lymphocytes. A number of observations from this study provide strong evidence that this is indeed the case.

The in vitro studies demonstrated that EtxB was able to induce the proliferation of primed lymph node cells. This property was not dependent on receptor binding, since responses with similar anamnestic characteristics were obtained using either wild type EtxB, EtxB(G33D) or heat-denatured monomeric forms of these proteins which cannot bind GM1. These observations are interesting in themselves since it has been widely reported that commercial preparations of Ctx and CtxB or purified recombinant CtxB are strongly inhibitory of lymphocyte proliferation in vitro. The apparent discrepancy may have arisen from the fact that previous experiments had been conducted on purified lymphocytes and had largely used mitogen stimulated lymphocyte cultures (which are not clonally restricted responses), where a different mechanism may be involved. Consistent with this was our observation that the proliferation of Con A-stimulated lymphocytes was indeed inhibited by EtxB. However, the analyses of cell populations in cultures of primed lymph node cells stimulated with either EtxB or EtxB(G33D) revealed important differences with respect to B cells as well as CD4 and CD8-bearing T-cells.

B cells were detected after 4 days of culture in the presence of either EtxB or EtxB(G33D). However, by comparison with EtxB(G33D), the relative proportion of B cells present in cultures with EtxB was increased by approximately 100%. This increase was associated with the expression of CD25 on a very high proportion of the B cells. In the experiment shown, the responding lymphocytes were primed with EtxB(G33D) in vivo. Similar experiments with cells from EtxB immunized mice revealed comparable results. Thus, irrespective of any in vivo effects associated with receptor binding, cultures in the presence of EtxB contained a larger proportion of B cells compared with those stimulated with EtxB(G33D). These effects on B cells also appear not to be dependent, at least in part, on regulation by T cells, in vitro, as the results do not suggest a major shift in the profile of the detected cytokines. Therefore, in vitro, receptor binding by EtxB appears to be associated with a direct effect on B cells, resulting in proportional expansion of this population as well as their activation. It is also noteworthy that CtxB has been shown to increase expression of MHC class II on virgin B cells, a property which was not exhibited by a GM1 binding mutant CtxB (G33E) (Francis, M. L., Ryan, J., Jobling, M. G., Holmes R. K., Moss, J, & Mond J. J. (1992) J. Immmunol. 148, 1999–2005). The results in these experiments suggest the presence of direct mitogenic effects by EtxB on antigen-primed B cells and demonstrate that such effects are mediated by receptor binding.

In addition to the effects of EtxB on B cells in culture, flow cytometric analyses reveal that this toxoid caused the complete depletion of any detectable $CD8^+$ cells. Once again, this effect was shown to be dependent on receptor binding, since this population of T cells were not depleted in cultures containing EtxB(G33D). Further, complete depletion of $CD8^+$ cells in cultures containing EtxB was observed, from mice immunized with wild type EtxB. There are three possible mechanisms by which such an effect may be mediated. 1) It is known that binding of Ctx or CtxB to GM1 on rat MLN cells induces patch and cap formation (Craig S. W. and Cuatrecasas P., (1975) Proc. Natl. Acad. Sci. USA, Vol.72, pages 3844–3848). It is possible that in this process EtxB-GM1 complexes and other molecules, including CD8, are internalized. Such a process would prevent flow cytometric detection of these cells using CD8 as a marker, and may result in their death due to the associated loss of the surface TCR complex. Although the latter may account for the absence of $CD8^+$ T cells in the culture, others found no loss of the TCR complex from the surface of human Jarkat T cell line when CtxB was used (Imboden, J. B., Shoback, D. M., Pattison, G, & Stobo, J. D. (1986) Proc. Natl. Acad. Sci. USA 83, 5673–5677). Absence of effects as a result of capping is supported by the finding that CD3 and CD4 markers were not affected. 2) An alterative mechanism would involve effects exerted by cytokines in culture. In this study, both IL-2 and IFN-γ were detected. The results, however do not suggest a major shift in the cytokine profile which would explain such a dramatic effect on $CD8^+$ T cells. 3) Absence of $CD8^+$ T cells may be due to active induction of apoptosis. Death of lymphocytes by apoptosis may involve capping as described above, or could be mediated in the absence of capping by effects on the signalling events in the cell. Activation-induced programmed death is dependent on $Ca^{2+}$ and involves phosphatases and kinases. Binding of CtxB to lymphocytes has been shown to inhibit protein kinase C-dependent proliferation and induced a pronounced increase in intra-cellular $Ca^{2+}$, events which were not associated with an increase in CAMP level. The ability of EtxB to deplete $CD8^+$, but not $CD4^+$ T cells could be due to differential effects of signals associated with the CD4/CD8-TCR complex, resulting from crosslinking GM1 on the surface of these subset of lymphocytes. This could be as a result of differential binding of the toxoid on the membrane as reported for CtxB or alternatively to the differential signalling mechanisms in $CD4^+$ and $CD8^+$ T cells.

In the complete absence of detectable $CD8^+$ T cells, EtxB increased the proportion of $CD4^+$ T cells which were activated, by comparison with the receptor binding mutant. The essential requirement for $CD4^+$ T cells in response to Ctx has been demonstrated in vivo. The reason for the increased activation of this T cell subset is, however, unclear. It is noteworthy that CtxB has been shown to stimulate DNA synthesis and cell division in quiescent non-transformed mouse 3T3 cells. A selective mitogenic effect on $CD4^+$ T cells was also found in the presence of plant lectins which bind to Galβ-1-3-3GalNAc, the same component that EtxB binds to in GM1. The possibility can not be ruled out that EtxB mediates a GM1-binding dependent direct effect on $CD4^+$ T cells, causing their activation. However, it is also possible that the increased activation of $CD4^+$ T cells in cultures containing EtxB is a consequence of those changes to the B cell and $CD8^+$ T cells populations described. B cell activation is known to be associated with an enhancement of their competency as antigen presenting cells for $CD4^+$ T cells. Further, $CD8^+$ T cells are widely associated with a regulatory role in immune reactivity both in vivo and in vitro. Their removal from T cell proliferative cultures has been associated with prolonged and enhanced levels of $CD4^+$ T cell division.

Taken together, the potent immunogenicity of EtxB in vivo, as shown in this study, can be suggested to occur as a result of its ability to increase activation of B cells exerted by growth regulating effects following binding to GM1. Activation of $CD4^+$ T cells and the ability of EtxB to increase production of IL-2 in culture in vitro may provide the necessary signal for further expansion of B cell clones. Depletion of $CD8^+$ T cells by EtxB in vitro in this study may also provide another mechanism of immunopotentiation in vivo following systemic or oral delivery, particularly in the light of the involvement of this subset of cells in suppression of the immune response and in oral tolerance. In this regard, both Ctx and Etx have been shown to abrogate oral tolerance to cofed soluble proteins and other studies implicated Ctx and CtxB depletion effects on intra-epithelial lymphocytes in the gut or in the dome of Peyer's patch to explain this mechanism. CtxB-inhibitory effects on $CD8^+$ T cells in vitro has also been shown to prevent graft versus host reaction.

In conclusion, it has been demonstrated that the presence of potent immunomodulatory effects by EtxB on the antibody response in vivo, and on populations of lymphocytes ir. vitro. Furthermore, it has been demonstrated that these effects are mediated by receptor binding. Our findings are also pertinent to an understanding of the ability of Etx and Ctx to act as potent adjuvants and as potential protein carriers for other antigens and suggest that such properties rely on the capacity of these toxoids to bind ganglioside receptors on the surface of lymphoid cells.

Example 2

This example illustrates that the effects on CD8 cells are irrespective of antigen recognition and are mediated by apoptosis.

Recombinant preparations of EtxB and EtxB(G33D) were prepared as in Example 1. Both proteins were well characterised with respect to binding to GM1, binding to a panel of monoclonal and polyclonal antibodies and various other physico-chemical properties. Ovalbumin (OVA) was purchased from Sigma (Poole, UK). Mesenteric lymph nodes (MLN) were isolated from BALB/c mice [high responder strain to EtxB (Nashar, T. O. and Hirst, T. R. 1995. Immunoregulatory role of H-2 and intra-H-2 alleles on antibody responses to recombinant preparations of B-subunits of *Escherichia coli* heat-labile enterotoxin (rEtxB) and cholera toxin (rCtxB). *Vaccine* 13:803.)] 8–10 weeks old. Mice were injected i.p. with 200 μg of OVA (Sigma) emulsified in incomplete Freund's adjuvant (Sigma). MLN were removed 10 days after injection, minced through a stainless steel mesh into HBSS (Flow, Irvine, UK). The recovered cells were washed in HBSS by centrifugation (500 g, 10 min, 4° C.) and resuspended in modified-Eagle's medium (Flow) containing 20 mM HEPES, 100 IU penicillin, 100 μg/ml streptomycin, 4 mM L-glutamine and $5 \times 10^{-5}$ M 2-mercaptoethanol (complete medium) to which 0.5% (v/v) of fresh autologous mouse serum was added. Cultures contained $2 \times 10^6$ viable cells/ml in 2 ml volumes in 24-well plates (Nunc, Roskide, Denmark) and were established in the presence of 100 μg/ml OVA (dialysed extensively in complete medium), either alone or with 40 μg/ml of EtxB or EtxB(G33D). Cultures were incubated at 37° C. in 5% $CO_2$ and 95% air for 5 days. At desired time points, 0.1 ml samples were removed from the cultures and transferred to 96 well U-bottomed plates (Nunc) and pulsed with 1 μCi/well of [$^3$H]thymidine (Amersham, UK) for 6 h before harvesting (Mach III harvesting 96; Tomtec, Orange, Conn.) and counting by standard liquid scintillation (1450 Micro b plus; LKB-Wallac, Turku, Finland). For flow cytometric analysis (Becton Dickinson, Erenbodegem-Aalst, Belgium) of T cells, cells were stained with the following rat antibodies (PharMingen, Cambridge, UK): FITC labelled anti-CD4 (RNRM4-5) or FITC-anti-CD8α (53-6.7) and with biotin-labelled anti-CD25 (IL-2Rα) (7D4) followed by Streptavidin-phycoerythrin. Additionally, for the biotin-labelled antibodies FITC-labelled Streptavidin was used. FACS analysis of recovered cells was performed on the peak day of proliferation (day 4), as determined by [$^3$H]thymidine incorporation.

For apoptosis assays, fresh MLN cells (MLNC) and splenic T cells (SPLTC) were isolated from BALB/c mice, 8–10 weeks old. MLNC comprising >90% $CD3^+$ T cells, as determined by flow cytometric analysis, were incubated for 2 h in petri dishes (Costar, Cambridge, Mass.) in complete medium containing 10% FCS, at 37° C. in 5% $CO_2$ and 95% air to remove adherent cells. The non-adherent fraction was subsequently pipetted off, pelleted and washed twice in HBSS before use. SPLTC were purified by negative selection using glass beads coated with normal mouse serum followed by rabbit anti-mouse γ-globulins as described (Wigzell, H. 1976. Specific affinity fractionation of lymphocytes using glass or plastic bead columns. *Scand. J. Immunol.* 5: (suppl.5) 23.). The selected population of T cells were >90% $CD3^+$ as determined by flow cytometric analysis.

$CD4^+$ and $CD8^+$ T cells were separated as follows: non-adherent MLNC were labelled with rat phycoerythrin-anti-mouse CD4 (4708-02) or FITC-anti-mouse CD8α (53-6.7) (PharMingen) and were then incubated with MACS colloidal super-paramagnetic microbeads conjugated with goat anti-rat IgG (H+L) F(ab')$_2$ (PharMingen), according to the manufacturer's instructions. These were applied to mini-MACS columns (Miltenyi Biotec, Bergisch Gladbach, Germany) in order to separate both positively (>99% pure) and negatively (>90% pure) selected populations of CD4 and CD8+ T cells, as determined by flow cytometric analysis.

Two methods were used for quantification of apoptosis: i) staining DNA with acridine orange to examine nuclear morphology and, ii) cell cycle analysis following staining DNA with propidium iodide and with either anti-CD4 or anti-CD8 antibodies. Cultures of $2 \times 10^6$/ml MLNC, SPLTC and fractionated MLNC were established in complete medium containing 10% FCS, in the absence or presence of 80 μg/ml of either EtxB or EtxB(G33D) and examined from 4 to 18 h. Following incubation, cells were pelleted, washed with HBSS and stained with 5 μg/ml acridine orange (Sigma). Thymocytes were isolated and treated in the absence or in the presence of $10^{-7}$M dexamethasone and used as a positive control for cells undergoing apoptosis. Nuclear morphological changes in lymphocytes were examined by conventional or confocal fluorescence microscopy (Leica TCS 4D). The proportion of $CD4^+$ and $CD8^+$ SPLTC in the sub-$G_0$/$G_1$ stage of the cell cycle was determined by flow cytometric analysis of the DNA content following staining with propidium iodide as described (O'Connor, P. M., Jackman, J., Jondle, D., Bhatia, K., Magrath, I. and Kohn, K. W. 1993. Role of p53 tumor suppressor gene in cell cycle arrest and radiosensitivity of Burkitt's lymphoma cell lines. *Cancer. Res.* 53:4776.). Cells isolated from 18 h cultures of SPLTC incubated alone or with 40 μg/ml EtxB or EtxB(G33D) were stained with FITC rat anti-CD4 or FITC-anti-CD8α. Stained cells were adjusted to $1 \times 10^6$/ml in cold HBSS containing 20 mM HEPES and 0.5 mM EDTA and were fixed with cold ethanol added dropwise. Then, 50 μg/ml propidium iodide and 40 μg/ml ribonuclease A (DNase free) were added, and the cells incubated for 1 h at room temperature. The relative intensity of DNA staining with propidium iodide in CD4 and $CD8^+$ T cells was determined by gating on cells co-stained with each mAB.

Figure 6:
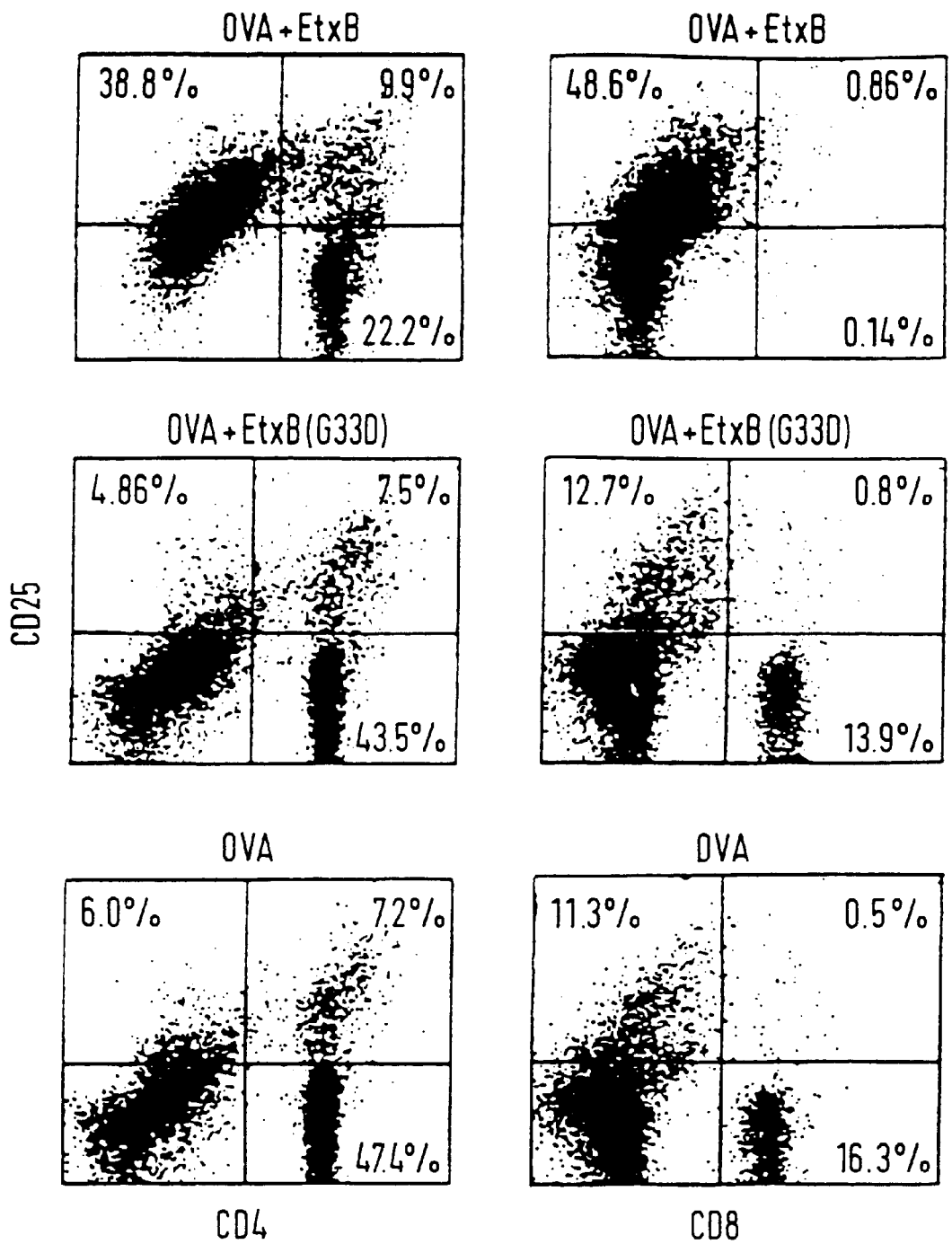
FIG. 6 shows the selective depletion of OVA-responsive $CD8^+$ T cells by EtxB.

In Example 1, the observation that $CD8^+$ T cells are completely depleted from cultures of lymph node cells proliferating in response to EtxB suggested that EtxB exerts a polyclonal effect on this T cell subset. To investigate whether such effects are dependent on the activation of EtxB responsive cells, cultures were established from OVA-primed mice and stimulated with OVA alone or with OVA plus either EtxB or the mutant EtxB(G33D). Similar peak levels of proliferation (day 4 of culture in each case) were achieved in the presence of OVA alone, OVA plus EtxB or OVA plus EtxB(G33D) (9734±347, 12,031±135 and 9305±290 c.p.m. respectively). However, there was a dramatic difference in the distribution of T cell subsets in these cultures after 4 days (FIG. 6). All cultures contained $CD4^+$ T cells of which similar proportions co-expressed the activation marker CD25. However, $CD8^+$ T cells were undetectable in cultures incubated with OVA plus EtxB, but were clearly present (although not activated as assessed by CD25 expression) in cultures with OVA plus EtxB(G33D) or OVA alone. This establishes that EtxB induces depletion of $CD8^+$ T cells responding to an antigen other than EtxB. Moreover, the absence of such a response to EtxB(G33D) indicates that depletion is triggered following toxoid receptor interaction. It was also noted that the presence of wild-type EtxB caused a significant increase in the proportion of B cells of which a large number were $CD25^+$ (not shown) as had previously been found for EtxB responsive cultures (Example 1). It is therefore concluded that receptor occupancy by EtxB exerts profound immunomodulatory effects on lymphocytes irrespective of their antigen specificity.

The possibility that CD8+ T cells undergo apoptosis when cultured in the presence of EtxB was investigated. MLNC or purified SPLTC, from unprimed mice, were incubated with EtxB or EtxB(G33D) and changes in cell nuclear morphology after staining with acridine orange were recorded over a period of 4 to 18 h (Table 3 and FIG. 7). Cell morphological changes were characterized by the presence of condensation of chromatin resulting in the lobular appearence of the nucleus (FIG. 7). Other cell features such as blebbing of the plasma membrane and the presence of apoptotic bodies were also observed. These morphological changes occurred in approximately one third of each of the cell preparations treated with EtxB, whereas a much lower incidence was observed in cells cultured with EtxB(G33D) or without exogenous antigen (Table 3). Since $CD8^+$ T cells accounted for ~35–40% of the MLNC and SPLTC preparations, depletion of these cells could account for the observed apoptosis. To establish if this was the case, populations of purified CD8 and $CD4^+$ T cells were cultured for 18 h in the presence of antigens (Table 3). Similar percentages of morphological changes were induced in negatively selected populations of $CD4^+$ T cells (containing >90% CD4-bearing cells) on treatment with either EtxB, EtxB(G33D) or no antigen, indicating that binding of EtxB to its receptor does not trigger apoptosis in this T cell subset. In contrast, >70% of the negatively selected $CD8^+$ T cells (>90% pure) exhibited morphological changes when cultured with wild-type EtxB; while incubation with either no antigen or EtxB(G33D) caused changes in only 11–19% of this T cell population, respectively. Further, the presence of low numbers of contaminating cells in the purified populations used (~10% in each case) could not account for the observed effects since more highly purified populations containing >99% of CD8 or $CD4^+$ T-cells (isolated by positive selection) responded to EtxB in a similar manner (60% were apoptotic in the presence of EtxB, compared with 7% for both no antigen and EtxB(G33D) treatments) (Table 3). Apoptosis was detected in 40% and 98% of thymocytes after 18 h incubation in the absence or in the presence of dexamethasone respectively.

To demonstrate that the morphological changes observed in our cultures were consistent with the induction of apoptosis, the appearance of subdiploid DNA in cultures of SPLTC treated for 18 h with EtxB was evaluated. Cells were subjected to flow cytomeric analysis after co-staining with propidium iodide and either anti-CD8 or anti-CD4 antibodies (FIG. 8). Approximately 48% of the $CD8^+$ T cells from cultures incubated with EtxB fell below the diploid $G_0/G_1$ peak of propidium iodide staining, indicating that they were undergoing apoptosis (O'Connor, P. M. et al, supra). A small proportion of cells expressing CD4, in cultures with EtxB, also exhibited sub-$G_0/G_1$ levels of DNA (~11%; which may result from the death of such a high proportion of $CD8^+$ T cells). In contrast, the majority of CD4 or $CD8^+$ T cells cultured without antigen or in the presence of EtxB(G33D) were in $G_0/G_1$ phase of the cell cycle, with <5% exhibiting apoptosis. We conclude that the observed nuclear morphological changes, and the presence of sub-$G_0/G_1$ levels of DNA, in a substantial proportion of $CD8^+$ T cells treated with EtxB demonstrate a selective apoptosis triggered by the cholera-like enterotoxoid. The failure of the receptor binding mutant, EtxB(G33D), to induce similar effects demonstrates that the induction of $CD8^+$ T cell apoptosis is linked to its ability to bind to GM1 ganglioside.

Example 3

Groups of 8 male DBA/1 mice were either unchallenged (group A) or were each injected with 100 $\mu$g of bovine collagen in CFA on day 0 by intra-dermal (i.d.) injection into the flank. Collagen injected mice were either left unprotected (group B; positive control) or attempts were made to prevent disease development by the administration i.d. at an adjacent site to collagen challenge of; 100 $\mu$g of EtxB in IFA on day 0 (group C), 100 $\mu$g of EtxB in IFA on day 14 (group D), or 100 $\mu$g EtxB(G33D) in IFA on day 0 (group E). All animals, except those in group A, received a boosting dose of collagen in IFA i.d. on day 21, and disease severity was assessed on day 45 by measuring hind limb ankle thickness (experiment A) or scoring each hind limb digit for swelling (scale 0–3 where 0=normal, and 3=maximal swelling; experiment B).

The results obtained are illustrated in FIGS. 9*a* and 9*b*. These show that EtxB, but not EtxB(G33D), dramatically protects mice from the development of collagen-induced arthritis.

Example 4a

Two separate human buffy coat samples (obtained from normal human blood donors) were used as a source of mononuclear cells. Cells were isolated over Ficoll-paque and washed extensively before culture in the absence of antigen or with 80 $\mu$g/ml of either EtxB or EtxB(G33D) as indicated. Prior to culture the cell populations comprised 24% CD8+, 27% CD4+ and 27% CD8+, 22.9% CD4+ for each sample respectively. After culture for 18 hours the appearance of apoptotic cells was assessed in samples of cells stained with acridine orange (as detailed under Example 2). The results obtained are shown in FIG. 10; these illustrate that EtxB but not EtxB(G33D) induces apoptosis in a population of normal human peripheral blood mononuclear cells.

Example 4b

The murine T cell line, CTLL-2, was cultured to confluence and then the cells washed before being reseeded at $1\times10^6$ cells/ml in the absence of antigen or with 80 $\mu$g/ml of either EtxB or EtxB(G33D) as indicated. After 18 hours samples were removed and the percentage of cells showing signs of apoptosis was assessed using acridine orange (detailed under Example 2). The results obtained are illustrated in FIG. 11. They show that cross-linking of GM1 leads to apoptosis in a proportion of murine CTLL cells.

TABLE 1

Lymphocyte proliferation in the presence of EtxB or EtxB (G33D)

| Dose μg/ml | EtxB | EtxB (G33D) | EtxB* | EtxB (G33D)* |
|---|---|---|---|---|
| 0 | 117.9 | 146.8 | 124.5 | 116.1 |
|  | (7.9) | (3.5) | (14.6) | (6.35) |
| 5 | 4928 | 2860 | 2424 | 1431.5 |
|  | (98.7) | (3.8) | (88.3) | (37.5) |
| 10 | 6978 | 3681 | 2518 | 4231 |
|  | (30.6) | (4.6) | (21.6) | (96.4) |
| 20 | 7084 | 6912 | 4394 | 5075 |
|  | (100) | (47.3) | (42.1) | (24.8) |
| 40 | 8844 | 8586 | 7431 | 4368.5 |
|  | (26) | (143.7) | (45.3) | (118.9) |
| 80 | 10246 | 12510 | 7986 | 7276 |
|  | (30.7) | (121.8) | (210.3) | (369.5) |
| 160 | 11311 | 13525 | — | — |
|  | (247) | (352.7) |  |  |

Mice were injected i.p. with 30 μg of EtxB (G33D) in complete Freund's adjuvant (CFA). Mesenteric lymph nodes were isolated 10 days later. Cells were isolated and incubated for 4 days in the presence of EtxB, EtxB (G33D) or disassembled monomeric forms of these proteins (*), generated by heating at 95° C. Proliferation was determined by addition of 1 μCi of ($^3$H) dThd for the last 6 hours on day 4. Data represents mean cpm and SEM of triplicate wells. Cells isolated form unimmunized mice gave <1500 cpm (dose 160 μg/ml).

TABLE 2

Cytokine analysis in the presence of EtxB or EtxB (G33D)

| Protein | IL-2 (pg/ml) | IFN-γ (pg/ml) |
|---|---|---|
| EtxB | 318 | 2700 |
| EtxB (G33D) | 67 | 4068 |

Mice were injected with EtxB (G33D) in CFA and mesenteric lymph nodes cells were isolated 10 days later. Cells were then incubated in vitro with either EtxB or EtxB (G33D) and samples of supernatants analysed for cytokine content on day 5 of cellular proliferation.

TABLE 3

EtxB-receptor mediated apoptosis in fractionated lymphocytes

| Cells | Time (h) | No antigen | EtxB (G33D) | EtxB |
|---|---|---|---|---|
| MLNC | 4 | 0$^a$ (8) | 2 (0) | 1 (3) |
|  | 18 | 8 (10) | 5 (18) | 29 (35) |
| SPLTC | 4 | 3 (7) | 2 (6) | 3 (5) |
|  | 18 | 17 (5) | 16.5 (12) | 31 (32) |
| Negative selection |  |  |  |  |
| CD4 | 18 | 5 (37) | 6 (31) | 9 (35) |
| CD8 | 18 | 18 (11) | 19 (15) | 76 (73) |
| Positive selection |  |  |  |  |
| CD4 | 18 | 6 | 4 | 6 |
| CD8 | 18 | 7 | 7 | 60 |

Nuclear morphological changes in fractionated CD4 and CD8$^+$ T cells after 4 or 18 h incubation in the absence of antigen, or with 80 μg/ml of EtxB or EtxB(G33D) were examined by fluorescence microscopy following staining with acridine orange. Whole MLN were depleted of adherant cells. SPLTC were isolated by negative selection in glass beads column coated with mouse γ-globulins and rabbit anti-mouse as a secondary antibody. Fractionated SPLTC were obtained following labelling with rat phycoerythrin-anti-mouse CD4 or FITC-anti-mouse CD8α which were then incubated with MACS colloidal super-paramagnetic microbeads conjugated with goat anti-rat IgG (H+L) F(ab')$_2$. These were separated using mini-MACS columns to obtain both the positively (>99% pure) and negatively (>90% pure) selected fractions of CD4 and CD8$^+$ T cells. Nuclear morphological changes were examined from 4 to 18 h in a random sample of 200 cells per treatment as described in the legend to FIG. 7. Maximum percentage of apoptotic cells occurred after 18 h. The data in brackets when indicated represent results from another separate experiment. Data for MLN and SPLTC are representative of a total of four experiments. $^a$Percentage apoptotic cells

What is claimed is:

1. A method for treating an autoimmune disease which comprises administering to a mammalian subject the B-subunit of E. coli heat labile enterotoxin (EtxB), having ganglioside GM-1 (GM-1) binding activity in an amount effective to treat the disease; wherein in vivo, the agent binds to GM-1; wherein the agent when bound to GM-1 has an effect on an autoimmune disease; and wherein, if the agent is co-administered with an antigenic determinant, then the agent and the antigenic determinant are not so linked as to form a single active agent.

2. A method according to claim 1 wherein the agent is co-adminstered with a self or cross-reacting antigenic determinant.

3. A method according to claim 1 wherein the agent is administered in a pharmaceutical composition which includes a pharmaceutically acceptable carrier or diluent.

4. A method according to claim 1 wherein the mammalian subject is human.

5. A method according to claim 1 wherein the agent is administered for the treatment of an autoimmune disease selected from the group consisting of rheumatoid arthritis, multiple sclerosis, and diabetes.

6. A method according to claim 1 wherein the agent is administered for the treatment or prevention of transplant rejection or graft-versus-host disease (GVHD).

7. A method according to claim 1 wherein the agent is administered for the treatment of human leukemias of a T cell origin.

* * * * *